(12) United States Patent
Prater et al.

(10) Patent No.: US 10,228,388 B2
(45) Date of Patent: Mar. 12, 2019

(54) METHOD AND APPARATUS FOR RESOLUTION AND SENSITIVITY ENHANCED ATOMIC FORCE MICROSCOPE BASED INFRARED SPECTROSCOPY

(71) Applicant: Bruker Nano, Inc., Santa Barbara, CA (US)

(72) Inventors: Craig Prater, Santa Barbara, CA (US); Kevin Kjoller, Santa Barbara, CA (US)

(73) Assignee: Bruker Nano, Inc., Santa Barbara, CA ( * ) Notice: Subject to any disclaimer, the term of this patent is extended or adjusted under 35 U.S.C. 154(b) by 0 days.

(21) Appl. No.: 15/348,848

(22) Filed: Nov. 10, 2016

(65) Prior Publication Data

US 2018/0120344 A1     May 3, 2018

Related U.S. Application Data

(60) Provisional application No. 62/414,707, filed on Oct. 29, 2016.

(51) Int. Cl.
*G01Q 30/02* (2010.01)
*G01N 21/35* (2014.01)
(Continued)

(52) U.S. Cl.
CPC ............. *G01Q 30/02* (2013.01); *G01N 21/35* (2013.01); *G01N 21/3563* (2013.01);
(Continued)

(58) Field of Classification Search
CPC ....................................................... G01Q 30/02
See application file for complete search history.

(56) References Cited

U.S. PATENT DOCUMENTS 8,248,448 B2   8/2012   Feng et al.
8,402,819 B2   3/2013   Dazzi et al.
(Continued)

OTHER PUBLICATIONS

Jahng J., et al et al., Photo-induced force for spectroscopic imaging at the nanoscale, Proc. SPIE 9764, Complex Light and Optical Forces X, (Mar. 4, 2016) 97641J ; doi:10.1117/12.2208199.
(Continued)

*Primary Examiner* — Eliza Osenbaugh-Stewart
(74) *Attorney, Agent, or Firm* — Boyle Fredrickson S.C.

(57) ABSTRACT

Methods and apparatus for obtaining extremely high sensitivity chemical composition maps with spatial resolution down to a few nanometers. In some embodiments these chemical composition maps are created using a combination of three techniques: (1) Illuminating the sample with IR radiation than is tuned to an absorption band in the sample; and (2) Optimizing a mechanical coupling efficiency that is tuned to a specific target material; (3) Optimizing a resonant detection that is tuned to a specific target material. With the combination of these steps it is possible to obtain (1) Chemical composition maps based on unique IR absorption; (2) spatial resolution that is enhanced by extremely short-range tip-sample interactions; and (3) resonant amplification tuned to a specific target material. In other embodiments it is possible to take advantage of any two of these steps and still achieve a substantial improvement in spatial resolution and/or sensitivity.

17 Claims, 12 Drawing Sheets

(51) Int. Cl.
*G01Q 60/34* (2010.01)
*G01N 21/3563* (2014.01)

(52) U.S. Cl.
CPC ..... *G01Q 60/34* (2013.01); *G01N 2201/0612* (2013.01); *G01N 2201/12* (2013.01)

(56) References Cited

U.S. PATENT DOCUMENTS

| | | | |
|---|---|---|---|
| 8,418,538 | B2 | 4/2013 | Dazzi et al. |
| 8,607,622 | B2 | 12/2013 | Dazzi et al. |
| 8,680,467 | B2 | 3/2014 | Prater et al. |
| 8,739,311 | B2 | 5/2014 | Wickramasinghe |
| 8,646,319 | B2 | 6/2014 | Prater et al. |
| 8,869,602 | B2 | 10/2014 | Belkin et al. |
| 8,904,561 | B2 | 12/2014 | Wickramasinghe |
| 9,046,492 | B1 | 6/2015 | Prater |
| 2012/0204296 | A1* | 8/2012 | Prater ............... B82Y 35/00 850/6 |
| 2013/0036521 | A1* | 2/2013 | Prater ............... B82Y 35/00 850/56 |

OTHER PUBLICATIONS

Rajapaksa, I et al. Image force microscopy of molecular resonance: A microscope principle. Appl. Phys. Lett 2010, p. 073121, vol. 97.

Nowak D, et al. Nanoscale chemical imaging by photoinduced force microscopy, Sci. Adv. 2016, p. 1-9., vol. 2 : e1501571.

Lu F, et al Tip-enhanced infrared nanospectroscopy via molecular expansion force detection, Nature Photonics 2014 p. 307-312, vol. 8.

Wickramasinghe H.K. et al, Force detection of IR response at sub-10nm resolution, SPIE Newsroom 2015 DOI 10.1117/2.1201511. 006170.

Huang F, et al Imaging Nanoscale Electromagnetic Near-Field Distributions Using Optical Forces., Sci Reports 2015 5:10610 | DOi: 10.1038/srep10610.

Jahng J. ,et al, Gradient and scattering forces in photoinduced force microscopy, Phys. Rev. B 2014, p. 155417 vol. 90.

Jahng J, et al, Linear and Nonlinear Optical Spectroscopy at the Nanoscale with Photoinduced Force Microscopy, Acc. Chem. Res., 2015, pp. 2671-2679 vol. 48 (10). DOI: 10.1021/acs.accounts. 5b00327.

Jahng J., Ultrafast pump-probe force microscopy with nanoscale resolution, Appl. Phys Lett 2015 p. 083113, vol. 106.

Jahng J. et al, Visualizing surface plasmon polaritons by their gradient force, Optics Letters 2015 p. 5058, vol. 40.

Yang H, et al, Resonant optical gradient force interaction for nano-imaging and -spectroscopy, New J. Phys. 2016 p. 053042, vol. 18.

Lu, F, et al, Infrared absorption nano-spectroscopy using sample photoexpansion induced by tunable quantum cascade lasers, Optics Express, 2011, p. 19942, vol. 19, No. 21.

Molecular Vista, undated product data sheet, "Vista Scope tip-enhanced nanomicroscopy/spectroscopy".

* cited by examiner

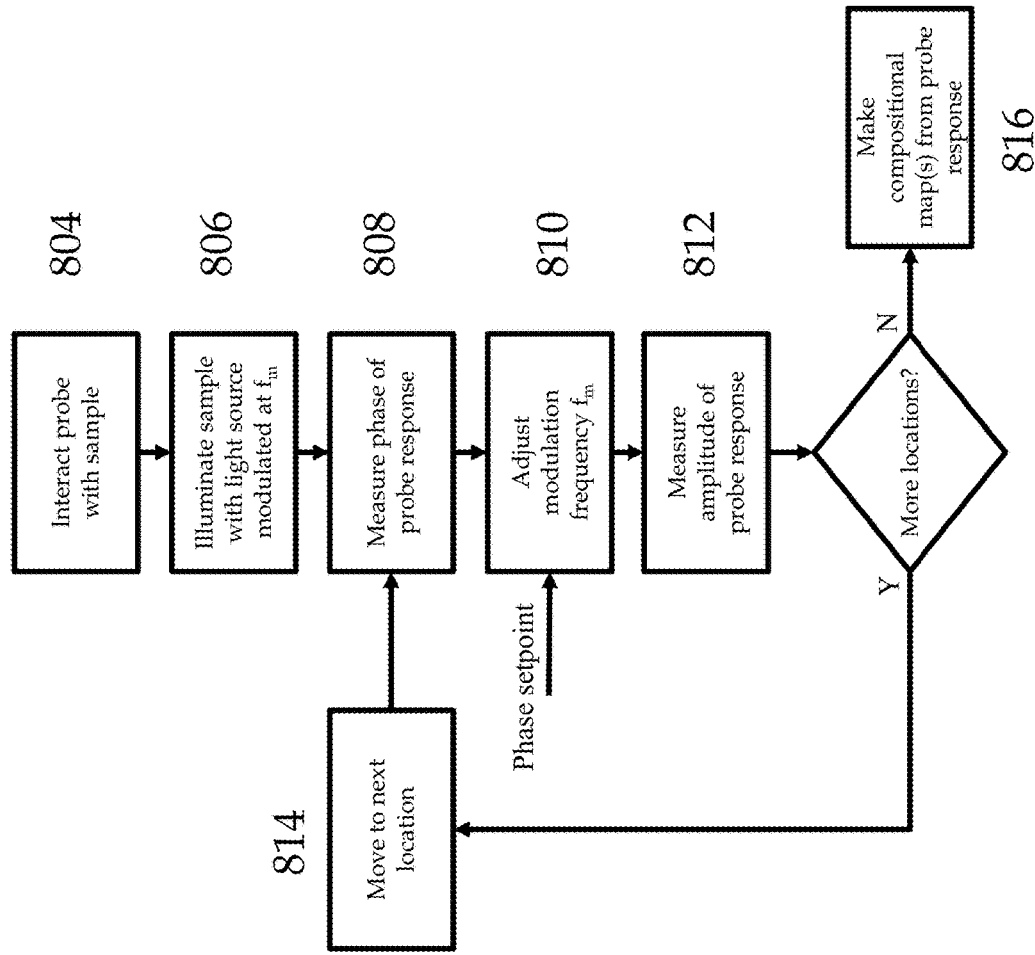
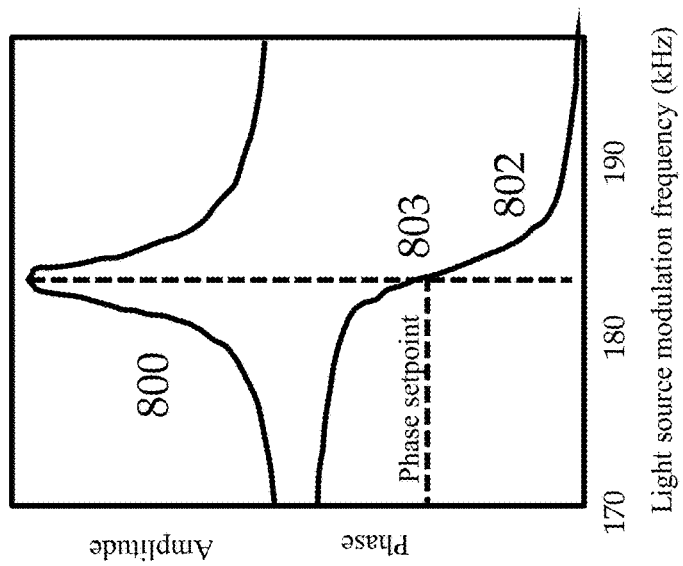

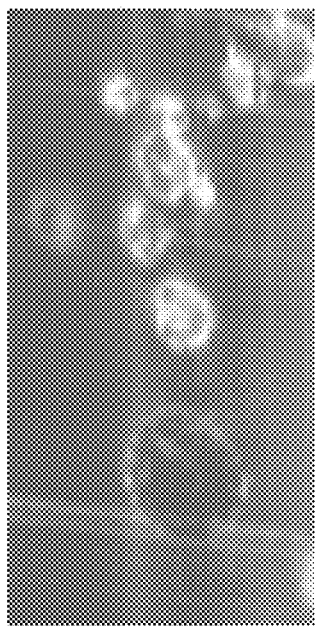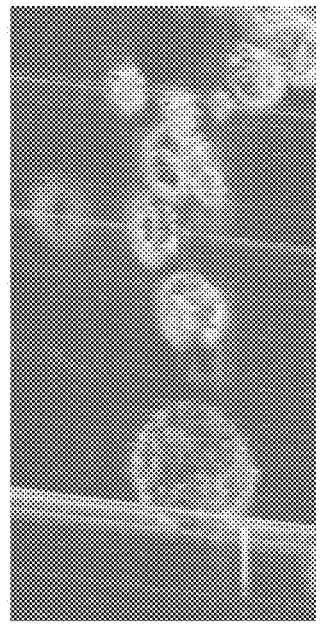
900  902
FIG. 9

METHOD AND APPARATUS FOR RESOLUTION AND SENSITIVITY ENHANCED ATOMIC FORCE MICROSCOPE BASED INFRARED SPECTROSCOPY

The specification relates to scattering Atomic Force Microscope based infrared spectroscopy (AFM-IR) in particular to for acquiring information indicative of the distribution of chemical components in heterogeneous systems.

AFM-IR may be a useful technique for measuring and mapping optical properties/material composition of some surfaces with resolution approaching nanometer scale. Various aspects of the technique are described in U.S. Pat. Nos. 8,869,602, 8,680,457, 8,402,819, 8,001,830, 9,134,341, 8,646,319, 8,242,448, and U.S. patent application Ser. No. 13/135,956, by common inventors and commonly owned with this application. These applications are incorporated by reference in their entirety.

BACKGROUND

Atomic force microscope based infrared spectroscopy (AFM-IR) provides chemical characterization and compositional mapping on nanometer length scales by using the tip of an atomic force microscope to locally detect absorption of infrared radiation.

SUMMARY

In some embodiments methods and apparatus are provided for obtaining extremely high sensitivity chemical composition maps with spatial resolution down to a few nanometers. In some embodiments these chemical composition maps may be created using a combination of three techniques: (1) Illuminating the sample with IR radiation than is tuned to an absorption band in the sample; and (2) Optimizing a mechanical coupling efficiency that is tuned to a specific target material; (3) Optimizing a resonant detection that is tuned to a specific target material. With the combination of these steps it may be possible to obtain (1) Chemical composition maps based on unique IR absorption; (2) spatial resolution that is enhanced by extremely short-range tip-sample interactions; and (3) resonant amplification tuned to a specific target material. In other embodiments it may be possible to take advantage of any two of these steps and still achieve a substantial improvement in spatial resolution and/or sensitivity.

In one embodiment of a first aspect, a method may be provided of mapping a surface of a heterogeneous sample with a probe of a scanning probe microscope, including the steps of: oscillating the probe at a first frequency $f_1$; interacting the probe with a first region of the sample; illuminating the sample with a beam of infrared radiation; modulating the beam of infrared radiation at frequency $f_m$ such that a resulting sideband frequency $f_{sb}$ is substantially equal to a resonance of the probe while interacting with a sample material at the first region; measuring a probe response at the first region of the sample at the sideband frequency due to infrared radiation incident on the sample; moving the probe to interact with a second region of a sample resulting in a shift in a resonance of the probe; retuning the modulation frequency $f_m$ resulting in a shifted sideband frequency that is substantially equal to the shifted probe resonance; measuring a probe response at the shifted sideband frequency on the second region due to infrared radiation incident on the sample. In another embodiment of the first aspect, the sample region is immersed in a liquid In one embodiment of the first aspect the method may further include the step of creating a compositional map of the sample based on the measured probe responses. In another embodiment of the first aspect the method may further include the step of creating a compositional map of the sample based on the measured probe responses. In another embodiment of the first aspect the method may further include the step of adjusting probe interaction parameters to substantially maximize a contrast between the probe responses on the first and second materials. In one embodiment of the first aspect the step of retuning the modulation frequency may be performed automatically. In one embodiment of the first aspect the compositional map may have a spatial resolution of <10 nm. In another embodiment of the first aspect the method may further include the step of measuring a phase of oscillation of the probe while the probe is in interaction with the sample region. In another embodiment of the first aspect the method may further include the step of using the phase measurement to adjust the radiation modulation frequency $f_m$. In one embodiment of the first aspect the frequency $f_1$ may substantially correspond to a probe resonance. In another embodiment of the first aspect the method may further include the step of adjusting a parameter of probe interaction to substantially maximize a contrast in the phase measurement between two or more material components in the sample.

In one embodiment of a second aspect, a method may be provided of mapping a surface of a heterogeneous sample with a probe of a scanning probe microscope including the steps of; oscillating the probe at a first frequency $f_1$; interacting the probe with a region of the sample; measuring a phase of oscillation of the probe while interacting with the sample region; adjusting one or more probe interaction parameters based on the phase measurement; illuminating the sample with a beam infrared radiation wherein the beam is modulated at a frequency $f_m$; tuning the modulation frequency $f_m$ such that a sideband frequency between $f_1$ and $f_m$ is substantially equal to a resonance of the probe while interacting with the sample region; measuring a probe response to infrared radiation incident on the region of the sample.

In another embodiment of the second aspect the method may further include the steps of repeating steps a-g on a second region of a sample comprising a second material component. In one embodiment of the second aspect the measured phase may be measured at frequency $f_1$. In one embodiment of the second aspect the probe microscope is operated in an amplitude modulation mode wherein feedback loop attempts to maintain an amplitude of probe oscillation at $f_1$ at a given setpoint amplitude. In one embodiment of the second aspect the probe interaction adjusting step may substantially maximize the measured probe response at the sideband frequency. In one embodiment of the second aspect the probe interaction adjusting step may substantially maximize a phase contrast between two or more material components in the sample. In one embodiment of the second aspect the measured phase may be measured at a sideband frequency between $f_1$ and $f_m$. In one embodiment of the second aspect the phase measurement may be performed at a sideband frequency between $f_1$ and $f_m$ and further comprising the step of tuning the radiation modulation frequency $f_m$ based on the phase measurement. In one embodiment of the second aspect the adjusting probe interaction parameters and tuning modulation frequency steps may be performed substantially simultaneously to compensate for shifts in probe resonance due to changes in probe interaction parameters. In another embodiment of the second aspect the method may further include the step of tuning an emission wavelength of the radiation source to substantially overlap with an absorption band of at least one material component in the sample. In another embodiment of the second aspect the method may further include the step of making a map of the distribution of at least one material component in the sample. In one embodiment of the second aspect the map may have a spatial resolution of less than 10 nm.

In one embodiment of a third aspect, a method may be provided of mapping a surface of a heterogeneous sample including the steps of: interacting a probe of a probe microscope with a region of the sample; illuminating the sample with a beam infrared radiation wherein the beam is modulated at a frequency $f_m$; measuring a phase of oscillation of the probe while interacting with the sample region; tuning the modulation frequency $f_m$ based on the phase measurement; measuring a probe response to infrared radiation incident on the region of the sample.

In one embodiment of the third aspect the probe may be oscillated at a frequency $f_1$ and the probe response may be measured at a sideband frequency between $f_m$ and $f_1$. In one embodiment of the third aspect the frequency $f_m$ may substantially correspond to a resonance of the probe. In one embodiment of the third aspect a phase locked loop may be used to adjust the modulation frequency $f_m$ based on the phase measurement wherein the phase measurement may be performed at a sideband frequency. In one embodiment of the third aspect the phase measurement may be used to adjust the modulation frequency $f_m$ to ensure that the sideband frequency substantially corresponds to a probe resonance. In another embodiment of the third aspect the method may further include the step of making a map of the distribution of at least one material component in the sample. In one embodiment of the third aspect the map may have a spatial resolution of less than 10 nm.

In one embodiment of a fourth aspect, a method may be provided of mapping a surface of a heterogeneous sample the method including the steps of: oscillating the probe at a first frequency $f_1$; interacting a probe of a probe microscope with a first region of the sample; illuminating the sample with a beam of infrared radiation; modulating the beam of infrared radiation at frequency $f_m$ such that a resulting sideband frequency $f_{sb}$ is substantially equal to a resonance of the probe while interacting with a sample material at the first region; measuring a probe response to infrared radiation incident on the first region of the sample at the sideband frequency; moving the probe to interacting with a second region of a sample; retuning the modulation frequency $f_m$ resulting in a shifted sideband frequency that is substantially equal to a resonance of the probe while interacting with a sample material at the second region of the sample; measuring a probe response to infrared radiation incident on the second region of the sample at the shifted sideband frequency.

In one embodiment of a fifth aspect, a method may be provided of mapping a surface of a heterogeneous sample the method including the steps of: oscillating the probe at a first frequency $f_1$; interacting a probe of a probe microscope with a first region of the sample; illuminating the sample with a beam of modulated radiation; selecting a set of material selective operating parameters to substantially maximize a probe response to radiation incident on the sample for a selected material component, wherein the material selective operating parameters comprise: wavelength of the radiation, radiation modulation frequency, and probe interaction parameters; measuring the probe response to radiation incident on the sample at a plurality of locations at optimized values of the material selective operating parameters; constructing a map of the distribution of the selected material component.

In another embodiment of the fifth aspect the probe interaction parameters may include at least one of: cantilever free oscillation amplitude, cantilever oscillation frequency, and cantilever amplitude setpoint. In one embodiment of the fifth aspect the map of the material component distribution may have a spatial resolution of <30 nm. In another embodiment of the fifth aspect the map of the material component distribution may have a spatial resolution of <10 nm. In one embodiment of the fifth aspect the sample region may be immersed in liquid. In one embodiment of the fifth aspect the probe may have a quality factor of 100 or greater. In one embodiment of the fifth aspect the region of the sample comprises material domains of <100 nm in lateral dimension. In another embodiment of the fifth aspect the method may further include the step of measuring probe response at a plurality of wavelengths of modulated radiation to construct a spectrum of an optical response of the region of the sample.

In one embodiment of a sixth aspect, an apparatus may be provided for mapping a surface of a sample with a scanning probe microscope including: a probe with a sharp tip: a radiation source; a radiation source modulator; a probe response detector; a lock-in amplifier; and, a processing element, the apparatus configured to interact the sharp tip with the sample surface direct a beam from the light source at a region of the sample in the vicinity of the probe tip; modulate the light beam at at least one frequency $f_m$; measure a response of the probe to radiation incident on the sample; determine at least one parameter of the probe response at at least one sideband frequency; automatically adjust at least one of: probe interaction parameter and modulation frequency $f_m$. In another embodiment of the sixth aspect the apparatus may further include a probe actuator configured to oscillate the probe at frequency $f_1$ and wherein the lock-in amplifier may be configured to determine a parameter of the probe response at a sideband frequency between $f_1$ and $f_m$. In one embodiment of the sixth aspect the apparatus may further include a phase locked loop configured to adjust $f_m$ such that a sideband frequency between $f_1$ and $f_m$ substantially corresponds to a probe resonance.

In one embodiment of a seventh aspect, an apparatus may be provided for mapping a surface of a sample with a scanning probe microscope including: a probe with a sharp tip: a radiation source; a radiation source modulator; a probe response detector; a phase detector; and, a processing element, the apparatus configured to: interact the sharp tip with the sample surface; direct a beam from the light source at a region of the sample in the vicinity of the probe tip; modulate the light beam at at least one frequency $f_m$; measure a response of the probe to radiation incident on the sample; measure a phase of the probe motion; automatically adjust at least one of: probe interaction parameter and modulation frequency $f_m$ based on the phase of the probe motion. In another embodiment of a seventh aspect the apparatus may further include a phase locked loop configured to use the phase detector to adjust $f_m$ such that $f_m$ substantially corresponds to a probe resonance. In one embodiment of a seventh aspect the apparatus may further include a phase locked loop configured to use the phase detector to adjust $f_m$ such that a sideband frequency between $f_1$ and $f_m$ substantially corresponds to a probe resonance. In one embodiment of a seventh aspect the phase detector may include a lock-in amplifier. In one embodiment of the seventh aspect the radiation source may include a broadband source. In another embodiment of the seventh aspect, the apparatus may further include an interferometer configured to demodulate the probe response as a function of wavelength.

BRIEF DESCRIPTION OF THE DRAWINGS

Aspects and advantages of the embodiments provided herein are described with reference to the following detailed description in conjunction with the accompanying drawings. Throughout the drawings, reference numbers may be re-used to indicate correspondence between referenced elements. The drawings are provided to illustrate example embodiments described herein and are not intended to limit the scope of the disclosure.

FIG. 8 illustrates a method for automated tracking of probe resonance and adjustment radiation modulation using a measurement of probe phase.

FIG. 9 shows measurement AFM-IR measurement results using the embodiment illustrated in FIG. 8.

DETAILED DESCRIPTION OF ILLUSTRATIVE EMBODIMENTS

Definitions

Figure 1:
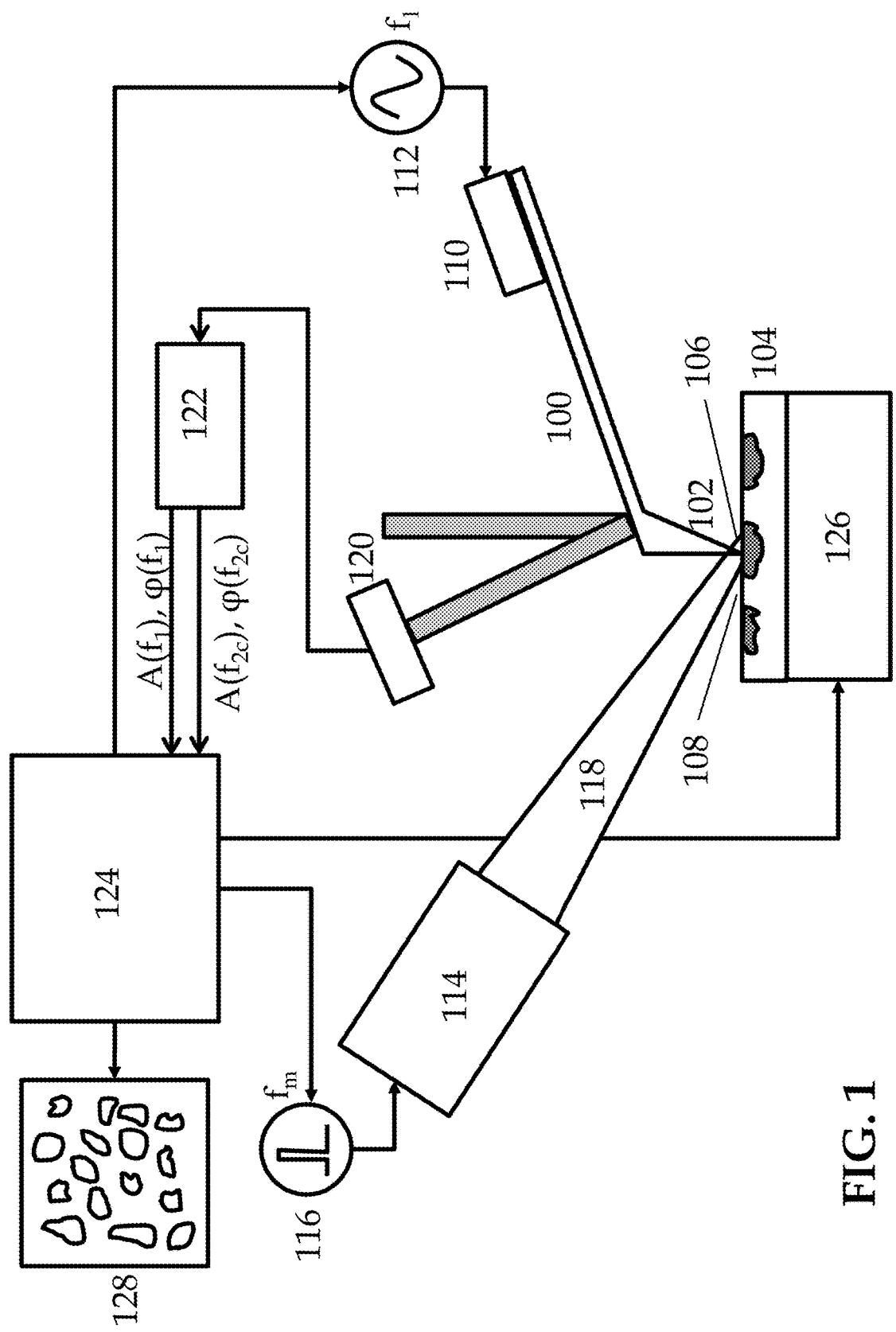
FIG. 1 shows a simplified schematic diagram of an illustrative embodiment.

"Interacting a probe with a sample" refers to bringing the probe tip close enough to the surface of a sample such that one or more near field interactions occur, for example the attractive and/or repulsive tip-sample forces, and/or the generation and/or amplification of radiation scattered from an area of the sample in proximity of the probe apex. The interaction can be contact mode, intermittent contact/tapping mode, non-contact mode, pulsed force mode, and/or any lateral modulation mode. The interaction can be constant or as in preferred embodiments, periodic. The periodic interaction may be sinusoidal or any arbitrary periodic waveform. Pulsed force modes and/or fast force curve techniques may also be used to periodically bring the probe to a desired level of interaction with a sample, followed by a hold period, and then a subsequent probe retraction.

"Illuminating" means to direct radiation at an object, for example a surface of a sample, the probe tip, and/or the region of probe-sample interaction. Illumination may preferably include radiation in the infrared wavelength range, but other wavelengths may also be used. Illumination may include any arbitrary configuration of radiation sources, pulse generators, modulator, reflecting elements, focusing elements and any other beam steering or conditioning elements. The radiation source may be one of a large number of sources, including thermal or Globar sources, supercontinuum laser sources, frequency combs, difference frequency generators, sum frequency generators, harmonic generators, optical parametric oscillators (OPOs), optical parametric generators (OPGs), quantum cascade lasers (QCLs), nanosecond, picosecond and femtosecond laser systems, CO2 lasers, heated cantilever probes or other microscopic heaters, and/or any other source that produces a beam of radiation. The source emits infrared radiation in a preferred embodiment, but it can instead or also emit in other wavelength ranges, for example from ultraviolet to THz.

"Spectrum" refers to a measurement of one or more properties of a sample as a function of wavelength or equivalently (and more commonly) as a function of wavenumber.

"Optical property" refers to an optical property of a sample, including but not limited to index of refraction, absorption coefficient, reflectivity, absorptivity, real and/or imaginary components of the index refraction, real and/or imaginary components of the sample dielectric function and/or any property that is mathematically derivable from one or more of these optical properties.

"Optical response" refers to the result of interaction of radiation with a sample. The optical response is related to one or more optical properties defined above. The optical response can be an absorption of radiation, a temperature increase, a thermal expansion, a photo-induced force, the reflection and/or scattering of light or other response of a material due to the interaction with radiation.

"Sideband frequency" refers to a frequency that is a linear sum or difference of two excitation frequencies. For example, if a system is excited at frequencies $f_1$ and $f_2$, a sideband frequency can be any frequency $f_{sb}$ that satisfies $f_{sb}=|\pm f_1 \pm f_2|$. More generally, in some cases a sideband frequency can also be a linear sum or difference of one of more harmonics of the excitation frequencies, i.e. $f_{sb}=|\pm mf_1 \pm nf_2|$, where m and n are integers.

"Signal indicative of" refers to a signal that is mathematically related to a property of interest. The signal may be an analog signal, a digital signal, and/or one or more numbers stored in a computer or other digital electronics." The signal may be a voltage, a current, or any other signal that may be readily transduced and recorded. The signal may be mathematically identical to the property being measured, for example explicitly an absolute phase signal or an absorption coefficient. It may also be a signal that is mathematically related to one or more properties of interest, for example including linear or other scaling, offsets, inversion, or even complex mathematical manipulations.

A "scanning probe microscope (SPM)" refers to a microscope where a sharp probe is interacted with a sample surface and then scanned the surface while measuring one or more properties of the sample surface. The scanning probe microscope may be an Atomic Force Microscope (AFM) which may include cantilever probe with a sharp tip. The SPM generally include a capability for measuring the motion, position and or other response of the probe tip and/or an object to which the probe tip is attached, e.g. a cantilever or a tuning fork or MEMS device, for example. The most common method includes using an optical lever system where a laser beam is bounced off the cantilever probe to measure deflection of the cantilever. Alternatives include self-sensing techniques like piezoresistive cantilevers, tuning forks, capacitive sensing and other techniques. Other detection systems may measure other properties such as force, force gradient, resonant frequency, temperature and/or other interactions with the surface or responses to the surface interaction.

"Cantilever probes" are generally microfabricated cantilevers made from silicon, silicon nitride or other semiconductor based materials. Probes have also been fabricated from metals and polymeric materials. In general, the probe only needs to have a sharp tip that can interact with the sample and support for some mechanism to detect the interaction, e.g. by the bending of the cantilever probe, or the change in resistance, resonance frequency or other property that is indicative of the interaction between the probe time and the sample.

A "scanner" is one or more scanning mechanisms used to generate relative translation between the probe and the sample so that the probe can interact with and measure properties of a plurality of positions on a sample. The scanning mechanism can move either the probe, the sample or a combination thereof. The scanning mechanisms are usually piezoelectric devices, but can also employ other mechanisms like electromagnetic, electrostatic, electrostrictive and other drive mechanisms that induce a desired motion in response to a given control signal or command. Scanners include, but are not limited to piezoelectric tubes, piezoelectric stacks, piezoelectric driven flexure stages, voice coils, and other mechanisms for providing precision translation.

An "SPM controller" refers to a system to facilitate data acquisition and control of the AFM-IR system. The controller may be a single integrated electronic enclosure or may comprise multiple distributed elements. The control elements may provide control for positioning and/or scanning of the probe tip and/or sample. They may also collect data about the probe deflection, motion or other response, provide control over the radiation source power, polarization, steering, focus and/or other functions. The control elements etc. may include a computer program method or a digital logic method and may be implemented using any combination of a variety of computing devices (computers, Personal Electronic Devices), analog and/or digital discrete circuit components (transistors, resistors, capacitors, inductors, diodes, etc.), programmable logic, microprocessors, microcontrollers, application-specific integrated circuits, or other circuit elements. A memory configured to store computer programs and may be implemented along with discrete circuit components to carry out one or more of the processes described herein.

A "lock-in amplifier" is a device and/or an algorithm that demodulates the response of a system at one of more reference frequencies. Lock-in amplifiers may be electronic assemblies that comprise analog electronics, digital electronics, and combinations of the two. They may also be computational algorithms implemented on digital electronic devices like microprocessors, field programmable gate arrays (FPGAs), digital signal processors, and personal computers. A lock-in amplifier can produce signals indicative of various metrics of an oscillatory system, including amplitude, phase, in phase (X) and quadrature (Y) components or any combination of the above. The lock-in amplifier in this context can also produce such measurements at both the reference frequencies, higher harmonics of the reference frequencies, and/or sideband frequencies of the reference frequencies.

Resolution and Sensitivity Enhanced AFM-IR

The current disclosure describes a method and apparatus for obtaining extremely high sensitivity chemical composition maps with spatial resolution down to a few nanometers. These chemical composition maps are created using a combination of three key techniques: (1) Illuminating the sample with IR radiation than is tuned to an absorption band in the sample; and (2) Optimizing a mechanical coupling efficiency that is tuned to a specific target material; (3) Optimizing a resonant detection that is tuned to a specific target material. With the combination of these steps it is possible to obtain (1) Chemical composition maps based on unique IR absorption; (2) spatial resolution that is enhanced by extremely short-range tip-sample interactions; and (3) resonant amplification tuned to a specific target material. One or more embodiments described herein may use all or in some cases any combination of two of these steps to achieve desirable results in spatial resolution and/or sensitivity.

FIG. 1 shows a schematic diagram of an embodiment of a resolution and sensitivity enhanced AFM-IR. A probe tip 102 of a scanning probe microscope is periodically interacted with a region 106 of a sample 104. In one embodiment, the probe comprises a cantilever 100 that is oscillated by an actuator 110 at at least one frequency $f_1$ driven by signal generator 112 The actuator is most commonly a piezoelectric element, but it can also comprise alternate drive mechanisms including magnetic, electrostatic, thermal, optical force or other schemes that apply an oscillatory force on the cantilever to drive it into oscillation. In one embodiment the frequency $f_1$ may be selected to correspond to a resonance of cantilever 100, but in other embodiments this is not necessary. A beam of infrared radiation 118 from an infrared light source 114 is used to illuminate a sample 104 in the vicinity of the tip 102 and the region of interest of the sample 106. In one embodiment, the probe response is measured via a deflection detection system 120, for example an optical lever system used to measure position, deflection, bend, and/or motion of the cantilever probe.

The illumination system may include any number of lenses, mirrors, attenuators, polarizers, beam steering elements to direct and condition the beam prior to arriving at the tip-sample region. In general, the light is focused to a spot, although in general the focused light spot is much larger than the tip-sample interaction region. The focusing optics may include lenses and or reflective focusing elements, for example parabolic mirrors, including off axis parabolic mirrors. The light, however, is often further "nanofocused" and/or intensified by the probe tip geometry and/or surface coating leading to an intensification of the electric field felt at the sample as a result of the incident radiation.

The radiation incident on the sample may interact with the sample and produce a detectable response. For example, if the wavelength of the IR radiation is tuned to an absorption band of the sample material, a portion of the incident radiation will be absorbed. The absorbed radiation can cause heating of the sample region, in turn resulting in a temperature rise and a thermal expansion of the absorbing region. The incident radiation may also induce a force on the probe tip, either through the thermal expansion and/or through interactions of the electric field of the probe and the electric field of the sample. In any case, a probe response can be measured in response to the radiation incident on the sample by one or more detections systems in the scanning probe microscope. The probe response can be elicited by measuring a temperature rise in the probe, a deflection, oscillation or force on the probe, for example. By changing the wavelength emitted from the radiation source to wavelength absorbed by another material component, it is possible to map the distribution of that component. Measuring the probe response at a plurality of wavelengths will result in a spectrum that is representative of the optical response of the sample, or in specific cases an IR absorption spectrum.

In one embodiment, the radiation beam 118 is modulated at at least one frequency $f_m$. This modulation may comprise an intensity modulation, an angle modulation or other modulation that creates a periodic variation in the strength of the radiation incident on the sample in the vicinity of the probe tip. The modulation may comprise a series of pulses or may be sinusoidal in nature or other arbitrary waveform shape with a periodic component at frequency $f_m$. In the case of a pulsed source, the modulation frequency $f_m$ can refer to the pulse repletion rate of the pulsed source. In one embodiment, the modulation may be accomplished for example by providing a modulation signal, a gating pulse, an external trigger or sync pulse to light source 114 that electronically modulates the intensity of the beam of radiation. Alternately, this modulation may be accomplished via an external modulator, for example a chopper, an electrooptic modulator, an electroacoustic modulator, a photoelastic modulator, an electronic shutter, a MEMS mirror, a high speed galvo, a piezo driven mirror or any other device that can periodically adjust the intensity and/or angle of a light beam that passes through the modulator. The light source may also be modulated by providing an analog modulation signal, for example to modulate the voltage and/or current provided to a light source, for example a quantum cascade laser.

In a specific embodiment a lock-in amplifier 122 can measure the oscillatory response of the probe 100, for example the amplitude and/or phase of the probe at a one or more frequencies, including the modulation frequency and/or one or more sideband frequencies. A controller 124 can read in data from the deflection detector 120, the lock-in amplifier 122 and other auxiliary signals as desired. The controller 124 can also output pulse to control the modulation of light source 114 or to an external modulator. Alternately it can simply send analog or digital commands to change the modulation rate of the light source. Controller 124 can also control the position of scanner 126 to control the relative tip/sample position. It can also be used to adjust any of the probe interaction parameters including the oscillation frequency (or frequencies) and amplitude(s) of the probe, the amplitude setpoint, scan speed parameters, feedback parameters, etc. It is understood that such a system includes one or more processing elements, shown as controller 124, but may in fact be distributed among a variety of processing elements including any combination of digital logic and/or computing devices connected to some or all of various actuators, sensors and user interface elements, displays, output devices and networks, wired and/or wireless. The system actions, data acquisition, and data processing described in this disclosure, in many cases, are the result of logical sequences and/or computer programs/applications executing on the processing elements.

Controller 124 can also provide computation and analysis on any of the input signals to produce a compositional map 128 based on the measured probe response. The compositional map is a map of the distribution of one or more material components in a heterogeneous sample. At any position on the sample it is also possible to obtain a spectroscopic measurement (i.e. measurements of the probe response as a function of wavelength or wavenumber). The spectroscopic analysis can be used to chemically characterize and/or identify materials at a given location. The combination of the spectroscopic measurements ("spectra") and the compositional maps can help users answer two critical questions: "What is it?" and "Where is it?" The spectra can be used to answer the "What is it?" question, i.e. the chemical composition of a region of the sample and the compositional maps can answer the "Where is it?" question, i.e. the distribution of one or more material components in a sample.

In one embodiment the probe response is detected at a "sideband frequency" that results from the nonlinear mixing of forces in the region of tip sample interaction that results in the generation of force components at sum and difference frequencies of the frequencies of tip and sample excitation. More specifically if the cantilever is oscillated at a frequency $f_1$ and the radiation incident on the sample is modulated at frequency $f_m$, in the presence of a non-linear mixing force, there will be frequency components at "sideband frequencies" $f_{sb}$, i.e. sum and difference frequencies, where $f_{sb}=|\pm f_1 \pm f_m|$. (Or more generally linear combinations any integer harmonics of these frequencies.)

The presence of probe response at sideband frequencies can come about by the following process. Consider a situation in which the tip-sample force has both linear and nonlinear terms based on the relative tip-sample separation. For example, to just quadratic terms, the tip sample force may be written as:

$$F_{ts} = -k_s(z_s-z_t) + \gamma(z_s-z_t)^2;\qquad\text{Eq. 1:}$$

where $k_s$ is the sample's linear contact stiffness, $z_s$ and $z_t$ are the sample position and the tip position respectively. The sample motion term $z_s$ is wavelength dependent and contains information about the sample's optical properties and/or IR absorption. The gamma term is the constant of proportionality to any quadratic dependence of the tip-sample force on tip-sample separation and as such is a term that is indicative of a nonlinear tip-sample interaction. (It is also proportional to the $2^{nd}$ derivative of the tip sample force with separation.)

If the motions of the tip and sample are periodic, the terms $z_s$ and $z_t$ will have Fourier components:

$$z_{s1}=a_s \cos(2\pi f_m t) \text{ and}\qquad\text{Eq. 2:}$$

$$z_{t1}=a_t \cos(2\pi f_1 t + \varphi_{ts});\qquad\text{Eq. 3:}$$

where $a_s$ and $a_t$ are the Fourier components of the tip and sample motion at the modulation frequency $f_m$ and the tip oscillation frequency $f_1$ respectively, and $\varphi_{ts}$ is the relative phase between the tip and sample motions. (If the motion of the tip and sample are non-sinusoidal, there will also be other Fourier components at higher harmonic frequencies, but we will omit them for simplicity in the current discussion.)

If we plug the values of $z_{s1}$ and $z_{t1}$ into Eq. 1 for $z_s$ and $z_t$, the quadratic term will be:

$$F_{ts2}=\gamma(z_{s1}-z_{t1})^2=\gamma(a_s \cos(2\pi f_m t)-a_t \cos(2\pi f_1 t+\varphi_{ts}))^2\qquad\text{Eq. 4:}$$

When multiplied out, Eq. 4 the tip-sample force will contains a cross-term $F_{ts\_sb}$:

$$F_{ts\_sb}=2\gamma a_s a_t \cos(2\pi f_m t)\cos(2\pi f_1 t+\varphi_{ts})\qquad\text{Eq. 5:}$$

This multiplication of the two cosines with create cross-terms (i.e. beat responses) at sum and difference frequencies of the tip and sample motion, i.e. at sideband frequencies $f_{sb}$:

$$f_{sb}=|\pm f_1 \pm f_m|\qquad\text{Eq. 6:}$$

The sideband force of Eq. 5 will provoke a response by the tip that is proportional to the force and the cantilever's response function at the given frequency. Specifically, the heterodyne probe response $r(f_{sb})$ at a given sideband frequency $f_{sb}$ can be approximated by:

$$r(f_{sb}) = 2\gamma a_s(\lambda) a_t H(f_{sb}) \qquad \text{Eq. 7:}$$

where $a_s(\lambda)$ is the amplitude of the sample motion at $f_m$, $a_t$ is an amplitude of the probe tip motion at frequency $f_1$, $\gamma$ is a nonlinear coupling coefficient, e.g. the quadratic coefficient in the tip sample force, and $H(f_{sb})$ is the value of the cantilever probe's response function at frequency $f_{sb}$. (Note that the equation above is written for sideband frequencies comprising linear combinations of the fundamental frequencies $f_1$ and $f_m$. In the case of using a sideband frequency corresponding to the use of a harmonic of either $f_1$ or $f_m$, the values of $a_s(\lambda)$ and $a_t$ correspond to the Fourier amplitudes at the harmonic frequencies, i.e. at $(m \times f_1)$ and $(n \times f_m)$ where m and n are integers. Note also that there are also similar formulations for the sideband response written in terms of forces instead of amplitudes.)

The term $a_s(\lambda)$ in Eq. 7 contains the wavelength dependent chemical/optical/spectroscopic information about the material under the tip. With this in mind we can consider the other terms constants of proportionality that we wish to optimize to maximize our sensitivity to the chemical/optical/spectroscopic information.

There are three key takeaways from Eq. 7:
(1) The probe response scales with both the sample motion and the tip motion $a_s(\lambda)$ and $a_t$.
(2) The probe response depends on the tip-sample force nonlinearity via nonlinear coupling coefficient $\gamma$.
(3) The probe response depends on the cantilever's response function $H(f_{sb})$ at the given sideband frequency $f_h$.

It should be noted that the dependence of the probe response to three of these terms are material dependent. By selecting system operating values, such as illumination wavelength, oscillation frequencies and amplitudes, probe characteristics, etc. to vary these material dependent terms appropriately, it is possible to create a measurement method that is extremely sensitive and highly selective for discriminating and mapping different materials. Specifically, a set of parameter value can be selected that provide a substantially maximum probe response for a specific material. We can then consider this set of selected parameter values as "material selective operating parameters," i.e. a set of parameter values that can be used to map the distribution of a target material with very high sensitivity and spatial resolution. Various techniques for achieving this are described below.

We now turn to the three different material dependent factors and how they can be maximized for a given material. First, the term $a_s(\lambda)$ is the sample motion. In the case that the wavelength of the infrared source is tuned to an absorbing wavelength of the region of the sample under the AFM tip, the absorbed radiation will cause heating and thermal expansion of the sample and thus a motion of the surface $a_s$. The sample motion term is maximized by selecting a wavelength corresponding to a strong absorption of the region of the sample under the AFM tip. Alternately, it may be selected to be a wavelength that has a maximal contrast in the absorptive properties between two or more component materials in the sample. (In a force based formulation of Eq. 7, there is a force based term equivalent to $a_s(\lambda)$ term that is related to the optical response of the sample at a given wavelength.) In any case, selection of an appropriate wavelength that generates a strong IR absorption and/or optical response is a first way to create a material selective probe response.

The second term that is material dependent is the nonlinear coupling coefficient $\gamma$. The nonlinear coupling coefficient is a measure of the degree of nonlinearity in the force interaction between the tip and sample. It can be sensitive to the material under the tip through a series of properties including the Hamaker constant, the viscoelasticity, friction, dissipation, adhesion, surface potential, hydrophobicity, and others, all of which can depend on the material composition and material properties. This factor is also heavily influenced by the details of the tip interaction with the surface. For example, it can be affected by both the free air amplitude of the oscillating cantilever and the amplitude of oscillation when the tip is interacting with the sample. (This is frequently referred to as the "amplitude setpoint" as a feedback loop is often used to maintain a desired level of interaction). Tapping mode AFM, for example can be operated in either attractive or repulsive regimes depending on free amplitude and amplitude setpoint, as described for example by Garcia (Phys. Rev. B 60(7) 1999). There is a strong dependence on the material dependent nonlinear coupling coefficient depending on which regime is employed. In the so-called attractive regime, generally characterized by a small free amplitude (~10 nm or less) and an amplitude setpoint close to the free air amplitude, the nonlinear coupling coefficient is small and not highly dependent on the material properties. In the so-called repulsive regime, generally characterized by a higher free amplitude (>10 nm typically) and/or an amplitude setpoint corresponding to a larger percentage reduction of the free air amplitude, the nonlinear coupling coefficient becomes much larger and can become highly material dependent. It has been determined that there may be a strong correlation between the amplitude of the probe response to incident IR radiation and the amount of phase contrast observed in AFM tapping mode phase imaging (as described for example in U.S. Pat. RE36,488). The apparent cause for the connection is the onset of nonlinear tip-sample forces that dramatically increase the non-linear coupling coefficient. As such, to maximize the degree of the nonlinear coupling coefficient it can be desirable to choose tapping mode operating conditions that show a strong phase contrast between different component materials in a sample. For a given material this operating point can also be found empirically by performing an amplitude/phase versus distance curve. As the oscillating AFM tip is approached to a sample surface, for sufficiently large free air amplitude there is an amplitude at which there is a phase discontinuity where the operating conditions switch from so called attractive to so called repulsive. By choosing a free air amplitude large enough to ensure that there is a phase discontinuity and an amplitude setpoint on the low side of the phase discontinuity, it is possible to find an operating point where the nonlinear coupling coefficient is much larger than in the attractive regime.

Figure 2:
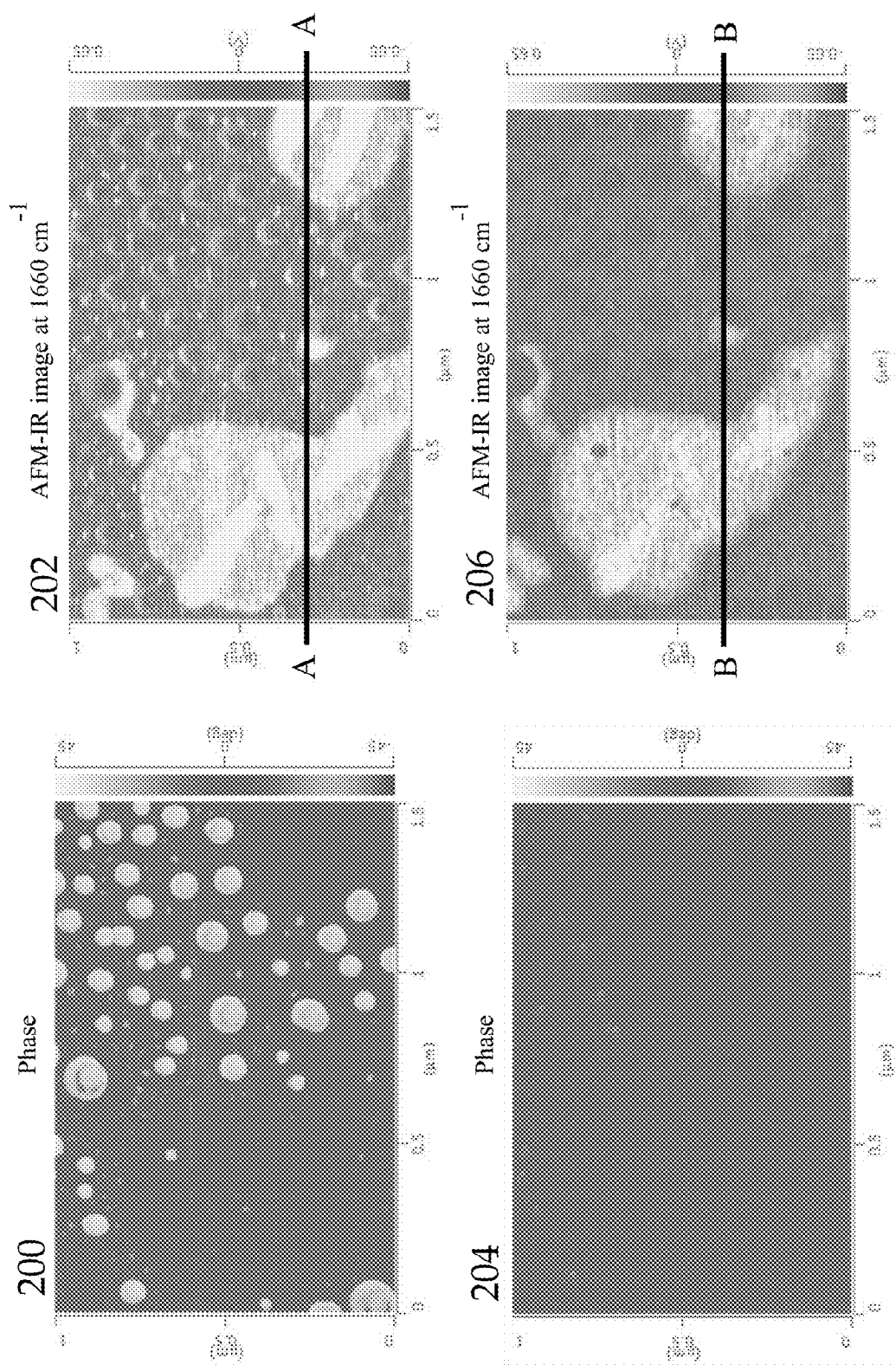
FIG. 2 shows an example of resolution enhanced measurements.
Figure 3:
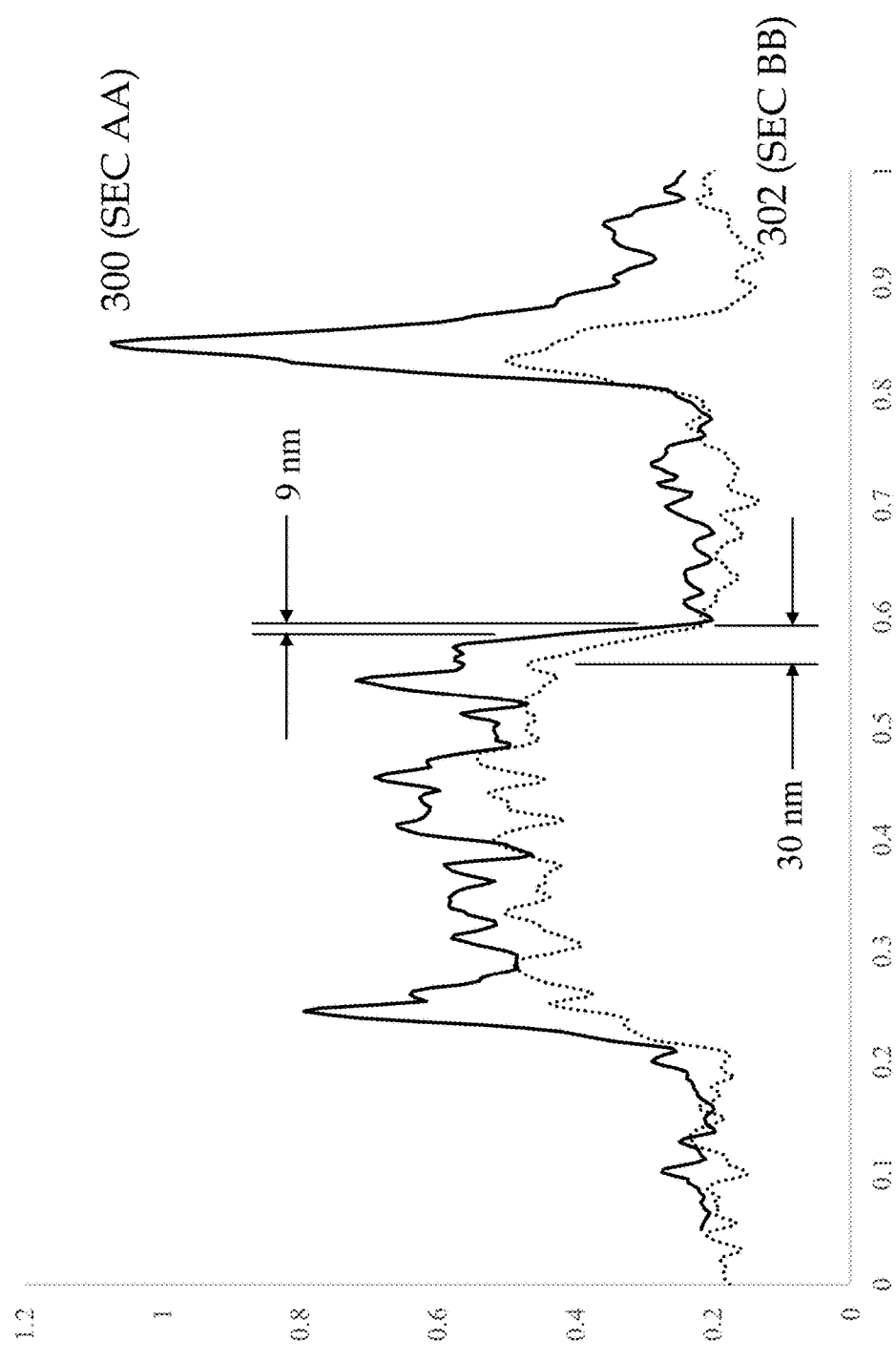
FIG. 3 shows cross-sections through measurements shown in FIG. 2.

There may be significant improvement in spatial resolution in AFM-IR images that are obtained in this operating regime. FIG. 2 shows an example measurement of a tapping AFM-IR measurements on a sample of purple membrane taken with the sample irradiated by a beam of radiation at 1660 cm$^{-1}$, corresponding to the Amide I absorption band in this biological membrane. The top images are respectively tapping phase image (200) and an AFM-IR image (202) taken under conditions that substantially maximize the phase contrast between the purple membrane and the adjacent gold substrate. The lower images are a tapping phase image (204) and an IR image 206 taken under conditions that minimize the phase contrast. Image 202 shows substantially improved spatial resolution under the condition that the contrast in the phase image is substantially maximized compared to 206. FIG. 3 shows cross-sections through the AFM-IR images. The cross-section 300 in FIG. 3 corresponds to the line section AA in FIG. 2 and the cross-section 302 in FIG. 3 corresponds to line BB in FIG. 2. These cross-sections allow comparison of the spatial resolution achieved under both operating conditions. On the same edge of the purple membrane path, we can compare the lateral distance over which the AFM-IR signal transitions from the baseline on the gold versus the signal on the purple membrane. Using 80%/20% vertical thresholds, section AA (solid, 300) shows a spatial resolution of roughly 9 nm, whereas the spatial resolution on section BB (dashed, 302) is around 30 nm. This shows a significant improvement in spatial resolution via the phase maximizing resolution enhancing scheme, and specifically a spatial resolution of less than 30 nm and preferably less than 10 nm.

Figure 4:
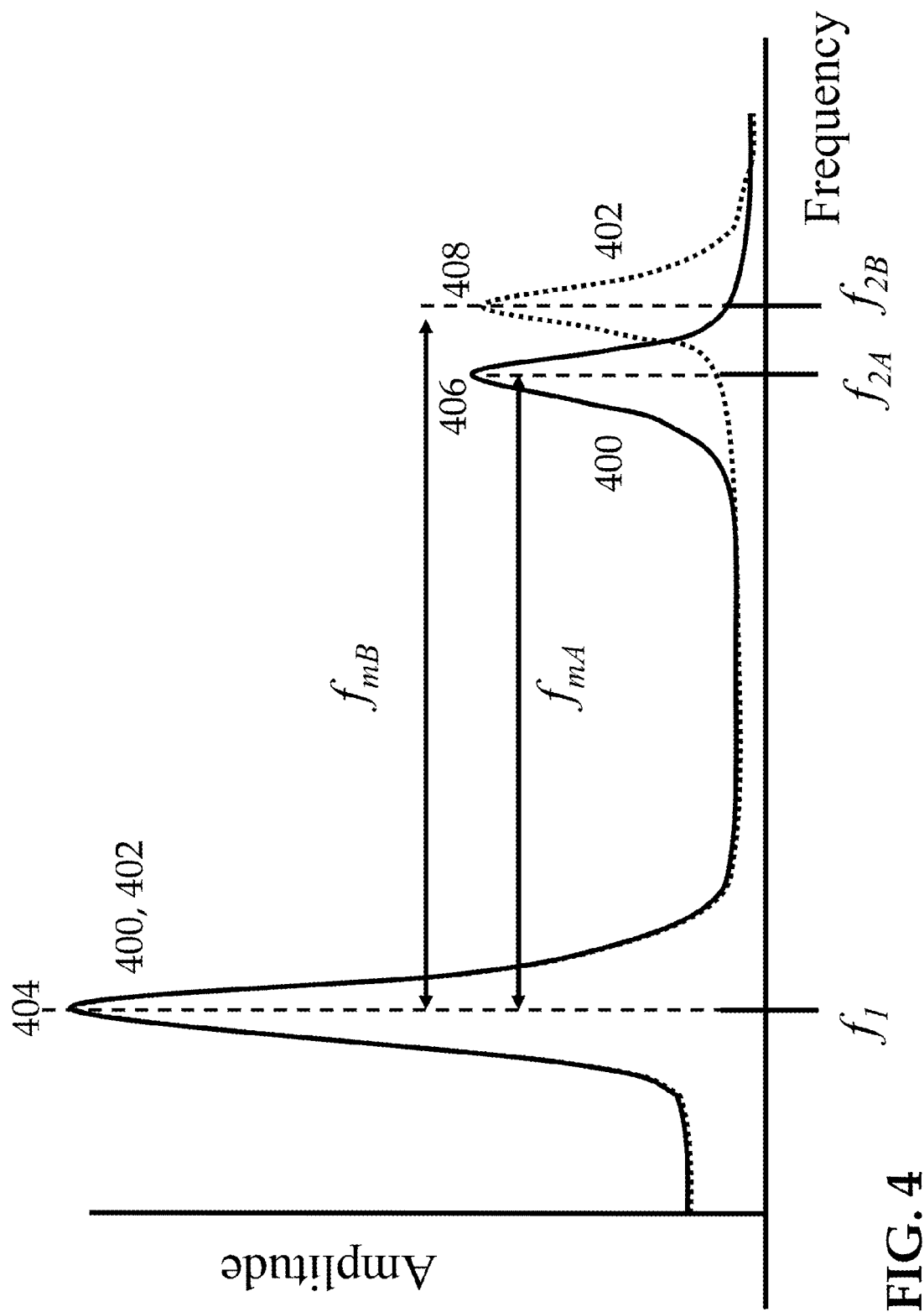
FIG. 4 illustrates material dependent shifts in probe resonances and shifts in modulation frequencies to account for such shifts.

The third material dependent factor that contributes to detected tapping AFM-IR signal is the cantilever transfer function $H(f_{sb})$ (400, 402), as illustrated in FIG. 4. The transfer function indicates the expected response of the cantilever to an excitation at a given mechanical frequency and as such shows peaks in response at each cantilever mode resonance. Two mode resonances are illustrated in each of the example transfer functions (400, 402) in FIG. 4. In one embodiment, the frequency $f_m$ is selected such that $f_m = f_{mA}$, so that the sideband frequency $f_{sb}$ created by the sum or difference of the cantilever oscillation frequency $f_1$ and the modulation frequency $f_{mA}$ substantially correspond to a resonance of the probe 100 when it interacts with a first material component A. That is:

$$f_{sb} = |\pm f_1 \pm f_{mA}| = f_{2A};$$

where $f_{2A}$ corresponds to a resonance of the probe 100 on material A. (As mentioned elsewhere, the sideband frequency can also be selected to be a linear combination of harmonic frequencies of f1 and fm. This can be advantageous especially in the case that one of the periodic excitations is non-sinusoidal and can have many Fourier components at higher harmonics.)

In the case that a sideband frequency corresponds to a resonance of the probe, the value of the probe transfer function $H(f_{sb})$ is at a local maximum 406 at frequency $f_{2A}$. On such a resonance, $H(f_{sb})$ is equal to the height of the local maximum peak 406 and in turn proportional to the probe's quality factor Q at $f_{2A}$. The Q factor of resonant modes of the cantilever in tapping can be quite high, from a few hundred to a few thousand. Probes based on tuning fork resonators, or cantilevers or other MEMS sensors in vacuum can be even higher in the range of 10,000 or more. This provides a dramatic enhancement of the detected signal strength.

The cantilever mode resonance frequency $f_2$ is typically not a constant value. In fact it can be highly material dependent as the sample properties affect the oscillatory properties of the cantilever. FIG. 4 shows an example of material dependent shifts in the $2^{nd}$ mode resonance of an AFM cantilever operating in tapping mode. The $2^{nd}$ transfer function 402 (dashed line) illustrates a shift in the higher mode resonance from $f_{2A}$ on material A (406) to a new frequency $f_{2B}$ (408) on material B. This shift in the probe response function provides an additional adjustable parameter to increase the material sensitivity, selectivity, and spatial resolution. To obtain an image with extremely high contrast between two or more materials, it may be desirable then to adjust the frequency of the light source modulation $f_m$ to specifically adjust for material induced shifts in the cantilever resonance $f_2$. The frequency $f_m$ in some cases can be adjusted to provide a maximal response for one material and a minimal response for another material. For example, consider the case where we measure the probe response to radiation incident on the sample at a sideband frequency $f_{sb}$ corresponding to the sum between $f_1$ and $f_m$. The laser modulation frequency $f_m$ can be tuned such that the sum frequency $f_{sb} = f_1 + f_m = f_{2A}$ where $f_{2A}$ is a cantilever resonance on material A. When the AFM tip is on material B, and the resonance frequency shifts to $f_{2B}$. If there is a sufficient material dependent difference between $f_{2A}$ and $f_{2B}$, then the sum $f_1 + f_m \neq f_{2B}$. In this case, the value of the cantilever transfer function $H(f_{sb})$ will be much smaller on material B, providing a much smaller or even negligible response. This provides a third way to maximize the sensitivity to a given material and to improve the spatial resolution for probe response images used to map the distribution of material components. The reason is that the probe response signal will decrease substantially as soon as the AFM tip moves onto a sample that shifts the cantilever mode resonances, decreasing the measured response at the sideband frequency.

Thus there are several material dependent factors that affect the probe response to incident IR radiation, outside the optical absorption properties of the sample. This issue provides both a problem and an opportunity. The problem is that these non-optical properties can offer the potential for misinterpretation of measured data. Imagine for example a measurement made of the probe response at a given wavelength of incident IR radiation across two or more materials that shows contrast in probe response over the different materials. While it may be tempting to ascribe the different in probe response to the difference in IR absorption at the given wavelength, the discussion above makes it clear that there are several other factors involved. For example, as illustrated in FIG. 4, it is possible for there to be a large enough material dependent shift in of a higher mode cantilever resonance such that if a $f_m$ is optimized for material A, that there will be little or no response on material B at the same frequency. So it is very possible to misinterpret an AFM-IR image to ascribe a difference in contrast to IR absorption where the actual source of contrast is mostly mechanical.

Figure 5:
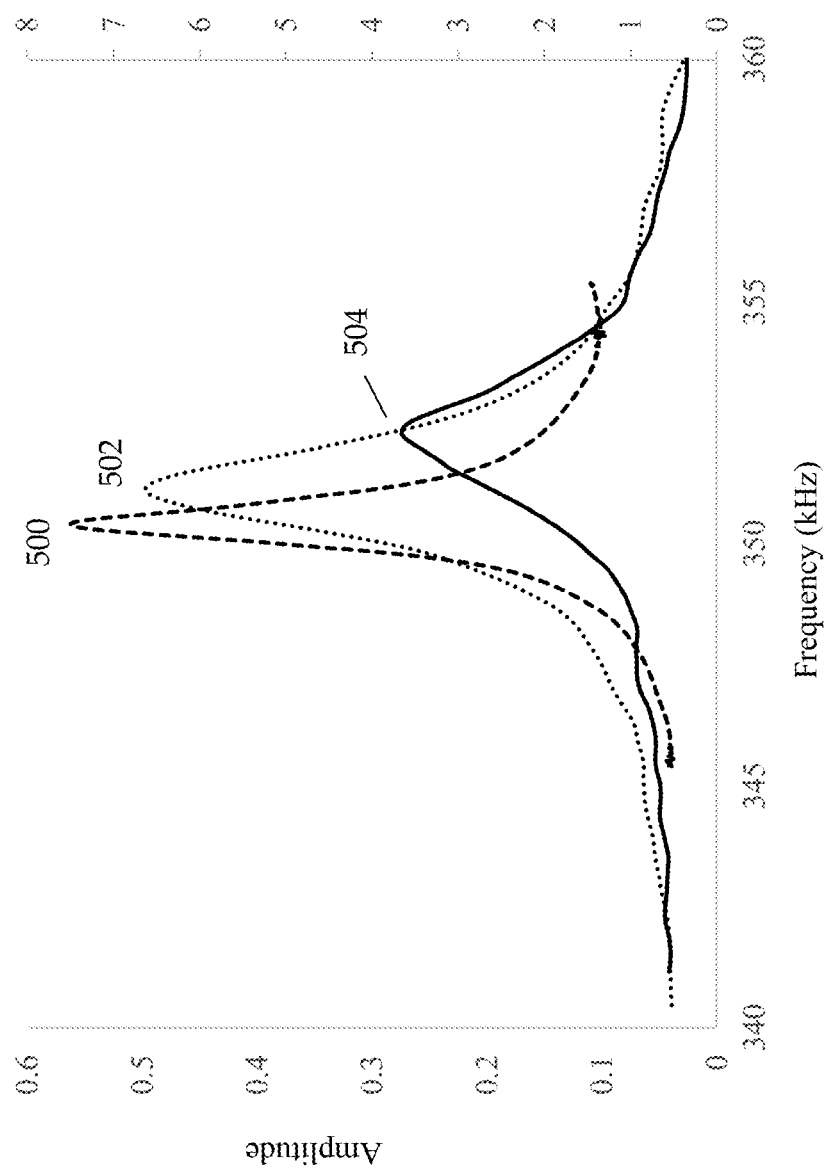
FIG. 5 illustrates material dependent shifts in probe resonance.

FIG. 5 demonstrates this issue in more detail. FIG. 5 shows the impact of interacting an oscillating probe tip with different materials on the $2^{nd}$ mode resonance peaks of a cantilever operating in tapping mode. Plot 500 shows the $2^{nd}$ mode resonance measured by oscillating the cantilever directly while not in interaction with the sample, i.e. it is a plot of the free resonance of the $2^{nd}$ mode of this cantilever. Plots 502 and 504 show AFM-IR sideband measurements where the frequency of the light source modulation is swept while the probe was interacted with two different material components in a polymer blend. (Note that the Y axis for plot 500 is at the right as the free air amplitude is much larger than the amplitudes while in tapping interaction.) For plots 502 and 504 the probe response measured was the sideband amplitude at the $2^{nd}$ mode resonance of a cantilever oscillated in tapping mode. That is, the measured response is due to the nonlinear mixing of the tip oscillation at $f_1$ and the light source modulation at $f_m$ while measuring the amplitude response at the sideband difference frequency $f_{sb} = f_m - f_1$. Note that there is an appreciable shift in the position of the $2^{nd}$ mode resonance between free air and interacting with the two polymer components. The free air peak in plot 500 is at 350.4 kHz, while the sideband peak amplitude on the first polymer component is in plot 502 is at 351.2 kHz, and at 352.4 kHz on the $2^{nd}$ material component in plot 504. Note first that there are frequency shifts for both materials relative to the free air oscillation. If one were to select a modulation frequency that generates a sideband frequency equal to a resonant frequency when the probe is not interacting with the sample, i.e. the peak of plot 500, it would not necessarily optimize the response for either material component which have different peak position in plot 502 and 504. That is, that selection of a modulation frequency that creates a sideband at the free cantilever resonance does produce a set of operating conditions that is highly material selective.

Plots 502 and 504 also show that there is a significant material dependent shift in the probe resonance frequency while the tip interacts with the two different material components in the polymer blend sample. These material dependent frequency shifts have the potential for producing measurement artifacts or significant misinterpretation of measured data. If for example, a user first interacted the sample with the second material and set the modulation frequency to the peak of plot 504, and then measured the probe response across the different materials, the user might see no difference in the probe response, due to the fact that the amplitudes of curves 502 and 504 intersect near the peak of 504. If the user concluded that there was no difference in material composition due to the similarity in probe response, this would clearly be incorrect as the first material in plot 502 has a much higher amplitude peak.

Similarly, it is possible to have frequency shifts when there is no change in the optical/absorption properties. In this case, a user might assume that there is a change in optical absorption, but instead the contrast may come just from differences in mechanical properties. It is also worth noting that an amplitude change can also result from a change in damping, resulting in a change in the quality factor Q of the resonance peak.

These issues may be avoided by techniques to (1) automatically setup and optimize sideband AFM-IR measurements; and (2) dynamically track and/or compensate for material dependent shifts that could otherwise cause artifacts or degradation in contrast.

Figure 6:
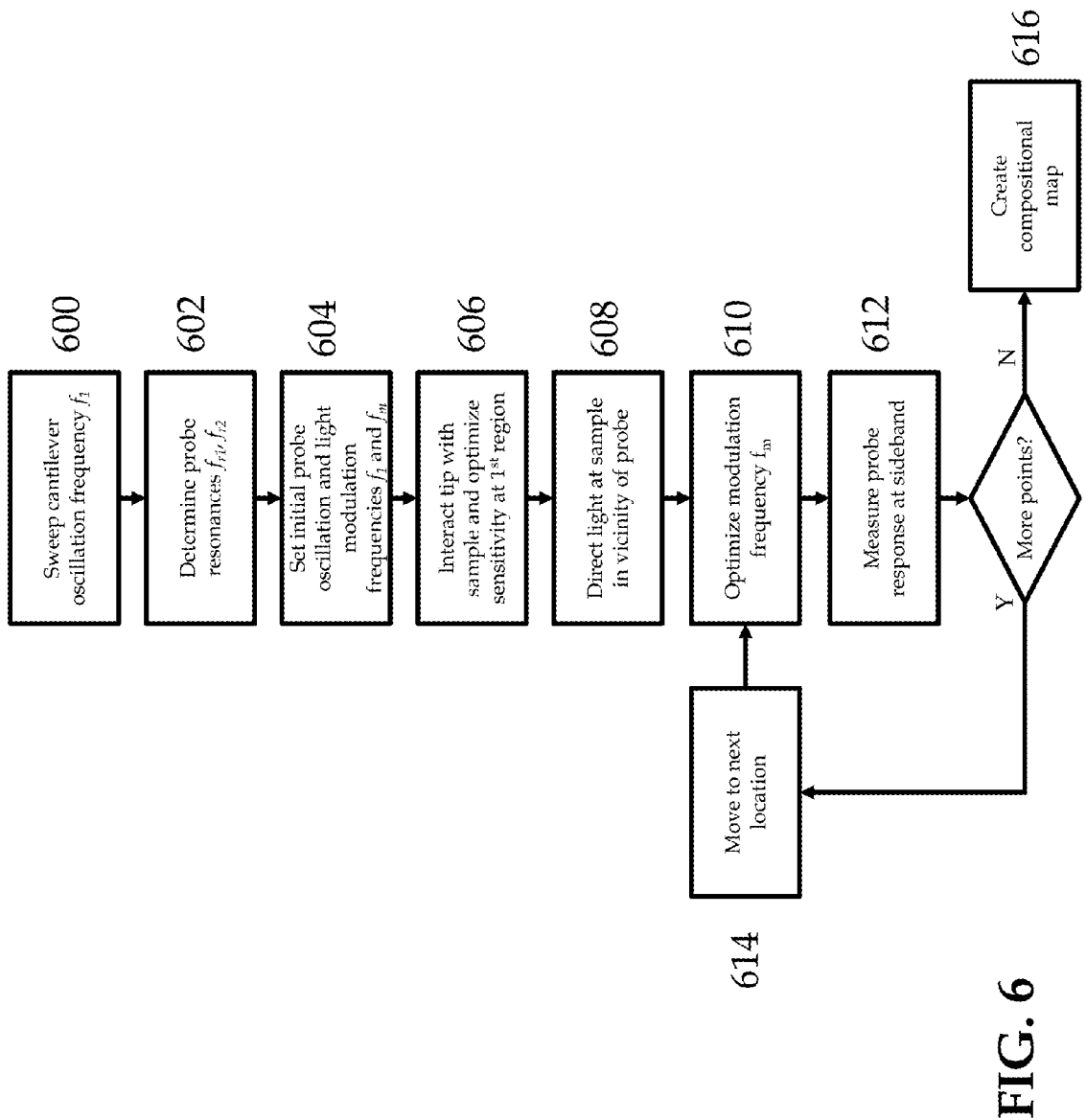
FIG. 6 illustrates a method for automatic setup and dynamic optimization of sideband probe response including automated tracking of a radiation modulation frequency to create a compositional map of a sample surface.

FIG. 6 illustrates a method embodiment used to setup, optimize and dynamically track material dependent shifts in sideband frequencies. In step 600, the cantilever probe is driven into oscillation with a direct excitation (e.g. with an actuator) while measuring the amplitude response of the probe. From this measurement, frequencies of probe resonances are determined, for example $f_{r1}$ and $f_{r2}$. In step 604, the initial setup is performed, for example setting the probe's first oscillation frequency $f_1$ near $f_{r1}$ and the radiation modulation frequency $f_m$ to generate a sideband frequency $f_{sb}$ between $f_1$ and $f_m$ to be substantially equal to $f_{r2}$. (Note that $f_{r2}$ need not be higher than $f_{r1}$. The cantilever can be operated in tapping mode at a higher mode frequency and the sideband response can be generated at a lower mode frequency if desired.) In step 606 the tip is brought into interaction with a sample surface at a first region and the probe-sample interaction is optimized. (Schemes for this optimization are described in more detail below and in the description of FIG. 7.) In step 608 modulated light is directed at the sample in the vicinity of the probe. The combination of this probe interaction with the surface and the light interaction with the surface can then generate a sideband response if there is a sufficient optical response in the sample at the selected wavelength of the light source. Because of the aforementioned shifts in the probe resonance while interacting with the surface, the initial setup of the system may not be optimal. So in step 610, the light source modulation frequency $f_m$ is adjusted to optimize the probe response at a given sideband. Then in step 612 a probe response is measured at a sideband frequency, either simultaneous with the optimization step 612 or subsequent to it. To create a composition map of the sample, the probe response can be measured at a plurality of positions. In step 614, the probe is moved to a next location on the sample surface and the modulation frequency can be re-optimized (610) to compensate for any material dependent shifts in the probe resonant frequencies. As described later in this specification, it is also possible to fix the modulation frequency to be highly selective and sensitive to a specific material component. This process can be repeated at multiple wavelengths of the light source to create a spectroscopic response of the samples over multiple regions of the sample. Alternately, it is possible to position the tip at a single location and rapidly sweep the wavelength of the light source while measuring the probe response to create point spectra that are indicative of the chemical composition and/or optical response of a region of the sample.

In one embodiment the light source modulation frequency $f_m$ can be dynamically adjusted to track any material dependent shifts in a higher mode resonance frequency. This can be accomplished in several ways. In one embodiment, the light source modulation frequency can be rapidly swept over a range of frequencies to determine the substantially maximum probe response for a given material. This can be performed as often as every image pixel. Alternately, it can be performed on select representative regions of the sample and then the modulation frequency $f_m$ can be dynamically adjusted when it is detected that the tip is on the specific material. This can be performed, for example using a tapping phase measurement or any other elastic, viscoelastic, friction, dissipation or other similar measurement that can be used to discriminate different materials. An algorithm can set a range of values for this auxiliary measurement that indicate that the measured signal is indicative of a specific material. For example, imagine that AFM phase imaging measurements indicate an average phase value of 35 degrees on material A and 45 degrees on material B. In a first step, we record the values of $f_m$ that correspond to maximal response on materials A & B. Then we perform a simultaneous tapping phase measurement and tapping AFM-IR measurement. We can set a transition point in the phase of 40 degrees (half way between 35 degrees for material A and 45 degrees for material B) as the threshold value to change the $f_m$ value. So for phase measurements below 40 degrees, the value of $f_m$ is set for a substantially maximum response for material A, and above 40 degrees it can be set to the maximum response for material B.

The above approach can be sufficient for mapping the material distribution for a limited set of material components with roughly uniform response across the individual components. But in the case of unknown components, or components with substantial heterogeneity, the above mentioned approach may not be sufficient. In an alternate embodiment the frequency $f_m$ may be automatically adjusted to maintain a substantially maximal probe response independent of the material using alternate means. For example, it is possible to measure one of more responses of the cantilever probe to adjust the modulation frequency to substantially maximize the probe response to incident radiation, even in the presence of different sample component materials that change the mechanical coupling factors. For example, it is possible to use a measurement of the phase of the probe response at a sideband frequency $f_{sb}$ as an indicator of shifts in a cantilever mode frequency. In fact, this signal can be used in a phase lock loop to dynamically adjust the light source modulation frequency $f_m$ such that the sideband frequency always corresponds to the resonance frequency of a selected cantilever mode. Other signals may also be used as indicators of mode resonances. For example, under some circumstances, the phase of the cantilever oscillator at its tapping frequency can provide an indicator of material dependent shifts in other mode resonances. It is also possible to mechanically excite additional higher mode resonances of the AFM cantilever probe and use the amplitude and/or phase of these resonances to infer shifts in the resonance frequency of the desired mode to which the sideband frequency is excited. For example, if the $2^{nd}$ mode resonance is selected for sideband modulation by the combination of cantilever oscillation at $f_1$ and laser sample irradiation at $f_m$, the $3^{rd}$ cantilever mode can be excited with a piezoelectric actuator and the phase of this mode can be monitored. Material dependent changes in the tip-sample interaction will cause a change in the phase response at the $3^{rd}$ mode and the amount of the phase change can be used to infer a change in the laser modulation frequency fm. Some level of calibration may be necessary to determine the correlation between phase changes at a higher mode resonance versus the change in the mode resonance selected for sideband excitation. Once the calibration is established it can be programmed into the control loop such that the system knows the amount of change in $f_m$ required to compensate for the measured change in a higher order phase.

Figure 7:
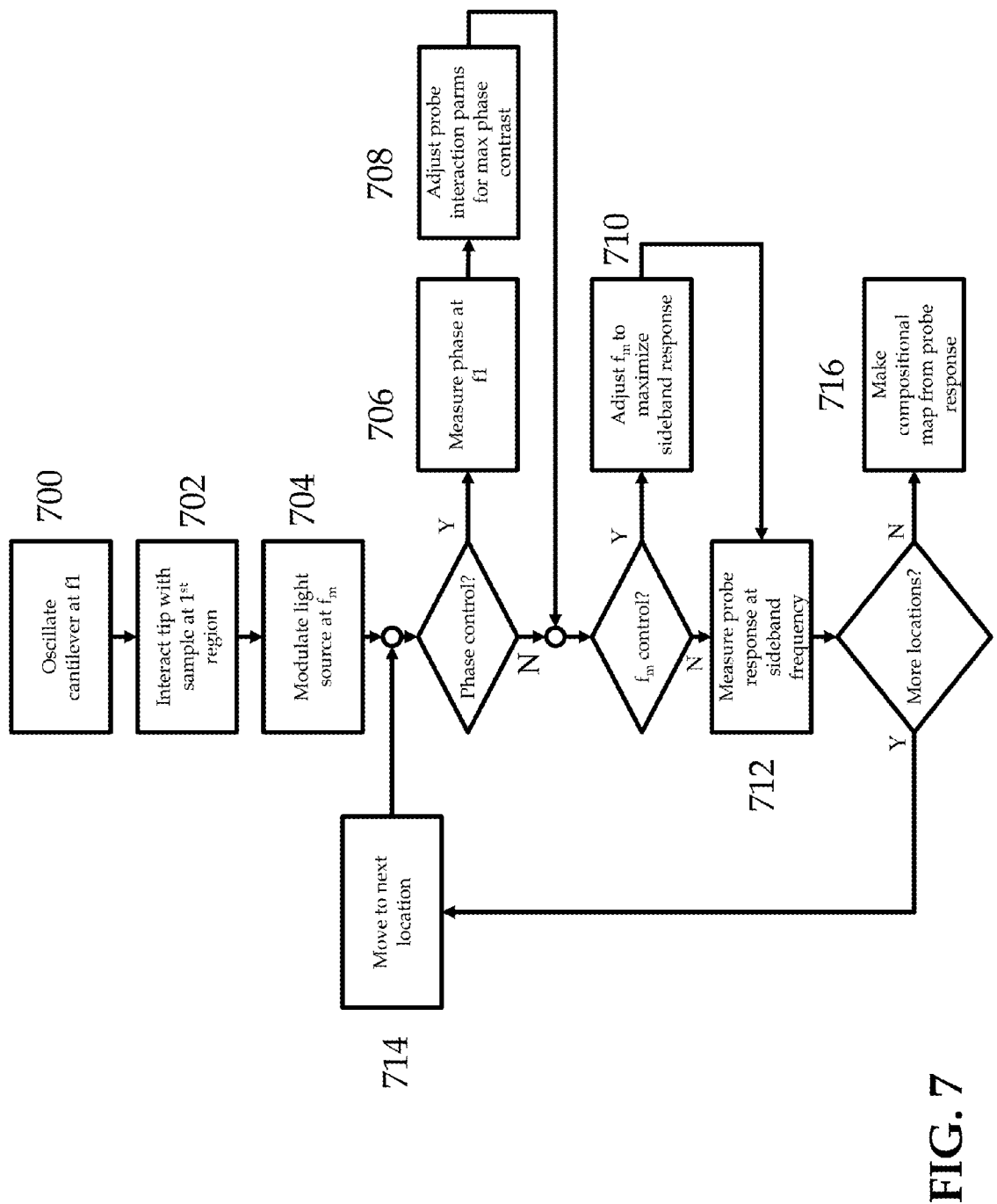
FIG. 7 illustrates a method for automated optimization of probe interaction parameters and radiation modulation frequency to create a compositional map of a sample surface.

FIG. 7 illustrates a method of obtaining high resolution, high sensitivity, and highly selective material composition maps:

Step 700: Oscillating the cantilever at a first frequency $f_1$.

Step 702: Interacting the probe tip with a first region of the sample.

Step 704: Modulating the light source at a frequency $f_m$.

Optional steps 706, 708: If phase control is enabled, the phase of the cantilever motion can be measured at frequency f1 (706) and the probe interaction parameters can be adjusted in response to the measurement (708). For example, parameters like the free air oscillation amplitude, the drive frequency $f_1$ and/or the amplitude setpoint can be adjusted to induce a desired phase response. In one embodiment, the probe interaction parameters can be adjusted to ensure that the probe is in repulsive tapping via identification of a phase discontinuity in the phase versus distance plot. Alternately, the probe interaction parameters can be adjusted to ensure a substantially maximum phase contrast between multiple material components in the sample. Alternately, the probe interaction parameters can be adjusted to achieve a substantially maximal difference in the phase of the cantilever oscillation at $f_1$ between when the probe tip is out of interaction with the surface versus in interaction with the surface.

Optional Step 710: If desired, the modulation frequency $f_m$ can be dynamically tuned or retuned to maximize material selectivity. Specifically, the modulation frequency $f_m$ can be set to a frequency to substantially maximize the measured probe response at a given sideband frequency. In practice, this involves tuning the modulation frequency $f_m$ such that the resulting sideband frequency corresponds to a resonance frequency of the probe. In this case, the probe response will be enhanced by the increase in the probe response when excited on resonance. In one embodiment the probe interaction parameters are adjusted substantially simultaneously with the tuning of the modulation frequency. In this case, the modulation frequency can be adjusted to track changes in the probe resonance that result from changes in the probe sample interaction.

Step 712: Then the probe response is measured at the first sideband frequency $f_{sb1}$.

Step 714: If there are more locations on the sample to be measured, the probe tip is then moved to a new location on the sample to repeat some or all of the steps mentioned previously. In the case that steps 706-708 are repeated, one or more probe interaction parameters are adjusted to maximize the nonlinear coupling coefficient for the new region of the sample. If step 710 is repeated, the radiation source modulation frequency $f_m$ is adjusted causing a shift in the resulting sideband frequencies. The value of $f_m$ can be retuned to result in a sideband frequency that is substantially equal to a probe resonance while interacting with the new region of the sample. The retuning process can happen on variable intervals. It can happen at each pixel in a compositional map (or multiple times per pixel), or it can also occur after every scan line or after an entire image, depending on the specific goal of the retuning.

Step 716: In one embodiment, the tip interaction parameters and the modulation frequency $f_m$ are not adjusted at the plurality of positions on the sample. In this case, the system will create a spatially resolved plot of the probe response at the sideband frequency where the system is highly optimized to detecting the presence of the first material for which the tip interaction parameters and sideband probe response was optimized. That is, this measurement will produce a strong signal wherever a target material is detected and a smaller or even negligible response where the material is not detected. The resulting image or map shows with very high selectivity and spatial resolution where the presence of a specific target material is, for example as shown in image 202 in FIG. 2. This process can then be repeated for a $2^{nd}$ material component and so on.

In alternative embodiments, one or more of the tip interaction parameters and the light source modulation frequency can be dynamically adjusted to compensate for any material dependent shifts in the optimal parameters. Specifically, the system can dynamically tune the drive amplitude or frequency at $f_1$, the amplitude setpoint at $f_1$ to achieve a desired phase response. The laser modulation frequency can also be tuned to compensate for material dependent shifts in the probe resonance frequency, i.e. to retune $f_m$ to ensure that it creates an updated sideband frequency that corresponds with any shifts in the selected cantilever mode resonance. In this case multiple images can be created simultaneously. First, an image of the probe response as a function of position on the sample can be created as before. Secondly, an image can be created that plots the frequency shift in $f_m$ as a function of position in the sample. This process has two advantages. First, the shifting of the laser modulation frequency $f_m$ reduces artifacts in the sideband probe response image that is solely due to variation in mechanical properties. Second, it provides a complementary data channel to measure and visualize these mechanical effects. So plotting the variation in $f_m$ across a plurality of locations on the sample allows for the visualization in the distribution of material components based on the mechanical properties, independently of the infrared absorptive properties of the sample.

Note that it is not necessary to adjust $f_m$ to be maximally on the resonance for either material A or B. Alternately, it is possible to select a modulation frequency $f_m$ that corresponds to a frequency where there is a substantially maximal contrast between the two materials. In this case, one desires to maximize the absolute difference in the cantilever response functions at a given frequency, i.e. finding the frequency $f=f_1+f_m$ (or other sidebands) that substantially maximizes the term $|H_A(f)-H_B(f)|$. This can be useful especially in the case that the cantilever quality factor is different on different materials such that the maximum value of $H(f)$ is different between the two materials.

Note that in the prior discussion is was mentioned that the first oscillation frequency $f_1$ need not correspond to a cantilever resonance. In a one embodiment the first oscillation frequency $f_1$ does correspond to a free resonance of the cantilever and the scanning probe microscope is operated in an amplitude modulation mode, commonly called tapping mode or intermittent contact mode. In another embodiment, the frequency $f_1$ can be at an alternative frequency off resonance. In this case the probe microscope can be operated in amplitude modulation mode, where the cantilever is oscillated at an additional modulation frequency. The probe microscope can also be operated in other modes, for example in contact mode, or in a fast force curve mode where the tip is repeatedly brought towards surface to a desired level of interaction. In this case the level of interaction can be selected to maximize the nonlinear coupling coefficient to maximize the probe response at the sideband frequency.

Is also possible to make measurements that essentially eliminate the contributions from the mechanical properties of the sample and the tip-sample interaction parameters. For independent measurements of the cantilever Q factor on different material components to compensate for damping dependent changes in the probe response. Measurements of Q coupled with dynamic shifting of the modulation frequency $f_m$ allow the probe response to be substantially a measurement of the optical response, minimizing contrast from mechanical property variations.

In alternate embodiments, it is possible to operate without the sideband detection. For example, as described in U.S. Pat. No. 8,680,457, it is possible modulate the radiation source directly at a frequency corresponding to a resonance of the cantilever probe. In this case, radiation incident on the sample can cause a direct excitation of the cantilever motion without the need for nonlinear mixing. In this case, however, the measurement sensitivity can be improved by active tracking of the cantilever resonance via a phase measurement or more specifically a phase locked loop. The phase of probe response due to incident radiation can be measured directly at the modulation frequency $f_m$ and this phase can act as an input to a feedback loop used to adjust $f_m$. In this way it is possible to dynamically adjust the laser modulation frequency to track any sample dependent variations in the cantilever resonance. This has the impact of maximizing the probe response to incident radiation independent of the material under the AFM tip. The phase locked loop can also operate in real-time pixel by pixel, eliminating the need to sweep the modulation over a range of frequencies (as is currently done in commercial AFM-IR systems operating in contact mode). Thus phase based tracking of the radiation modulation frequency can provide a substantial improvement in measurement speed. For example, to sweep over a plurality of frequencies to determine the peak amplitude, it is typically necessary to take measurements at 10-50 or more different frequencies to be able to find the peak and measure its center frequency with sufficient accuracy. With the phase tracking scheme, measurement can be made rapidly, limited only by the integration time needed for sufficient signal to noise over a single pixel. The phase tracking can proceed in parallel with the scanning processing, updating the modulation frequency continuously without the need for broad wavelength sweeps. A suitable phase tracking system can adjust the light source modulation frequency every 20 usec. Under this scheme, optical absorption and resonance frequency images can be obtained in as little as a few minutes, e.g. <5 minutes for a 200×200 pixel image.

This method is illustrated in FIG. 8. This scheme works because of a relationship between the phase and the amplitude of the probe response in the vicinity of a probe resonance. FIG. 8A shows a plot of a cantilever oscillation amplitude 800 and phase 802 as a function of the light source modulation frequency. This measurement was performed with an AFM cantilever in contact mode where the cantilever had a contact resonance around 183 kHz. In this plot the phase signal 802 has a relatively steep region 803 where the amplitude curve 800 has a resonant peak. It is then possible to maintain the light source modulation frequency at the peak of the amplitude resonance with a feedback loop that adjusts the modulation frequency to maintain a desired phase.

FIG. 8B shows a method of achieving this phase based control of the modulation frequency. In step 804 the probe is brought into interaction with the sample surface. In step 806, the sample is illuminated with a beam of radiation modulated at an initial modulation frequency $f_m$. Next, in step 808 a phase of the probe response is measured. In one embodiment, this is the phase at the modulation frequency, but it can also be a phase at a sideband frequency. Next the measured phase is compared to a phase setpoint and in step 810 the modulation frequency $f_m$ is adjusted. This can be performed by a PID loop or other means to attempt to keep the phase at or near the target value. In step 812, the amplitude of the probe response is also measured. This amplitude measurement can be performed concurrently with the phase measurement or after the modulation frequency is adjusted. This process is repeated by moving to a plurality of locations on the sample in step 814. A compositional map of the sample can be made (step 816) based on the probe response. This compositional map can comprise information from the amplitude measurement, the phase measurement, the modulation frequency or any combination thereof or any other measurement of the probe response. The amplitude measurement will be related to the optical absorption of the sample surface at a given wavelength of the radiation source. The frequency signal, which corresponds to the frequency of the probe resonance, is related to the sample stiffness. As such, multimodal measurements can be performed, obtaining both chemical and mechanical property measurements simultaneously. This process can be used in either contact mode, where the probe resonances correspond to contact resonances or in amplitude modulation where the probe resonances are essentially free oscillation resonances though modified by material dependent tip-sample interactions. And as mentioned above, this method can be applied directly to probe responses measured at the modulation frequency, at harmonics thereof or sideband frequencies due to nonlinear interactions with other probe/sample oscillations.

FIG. 9 shows an example of measurements performed according to the embodiment illustrated in FIG. 8. In these measurements a feedback loop was used to adjust light source modulation frequency $f_m$ to attempt to keep a phase of the cantilever oscillation at a target setpoint value. Image 900 is a contact resonance image obtained under these conditions while image 902 shows the amplitude of the probe response to the incident radiation at the given modulation frequency. In effect, the top image 900 is a plot of the relative stiffness of the sample and the bottom image 902 is a plot of the optical absorption. The sample is a blend of polystyrene and PMMA beads in an epoxy matrix.

Figure 10:
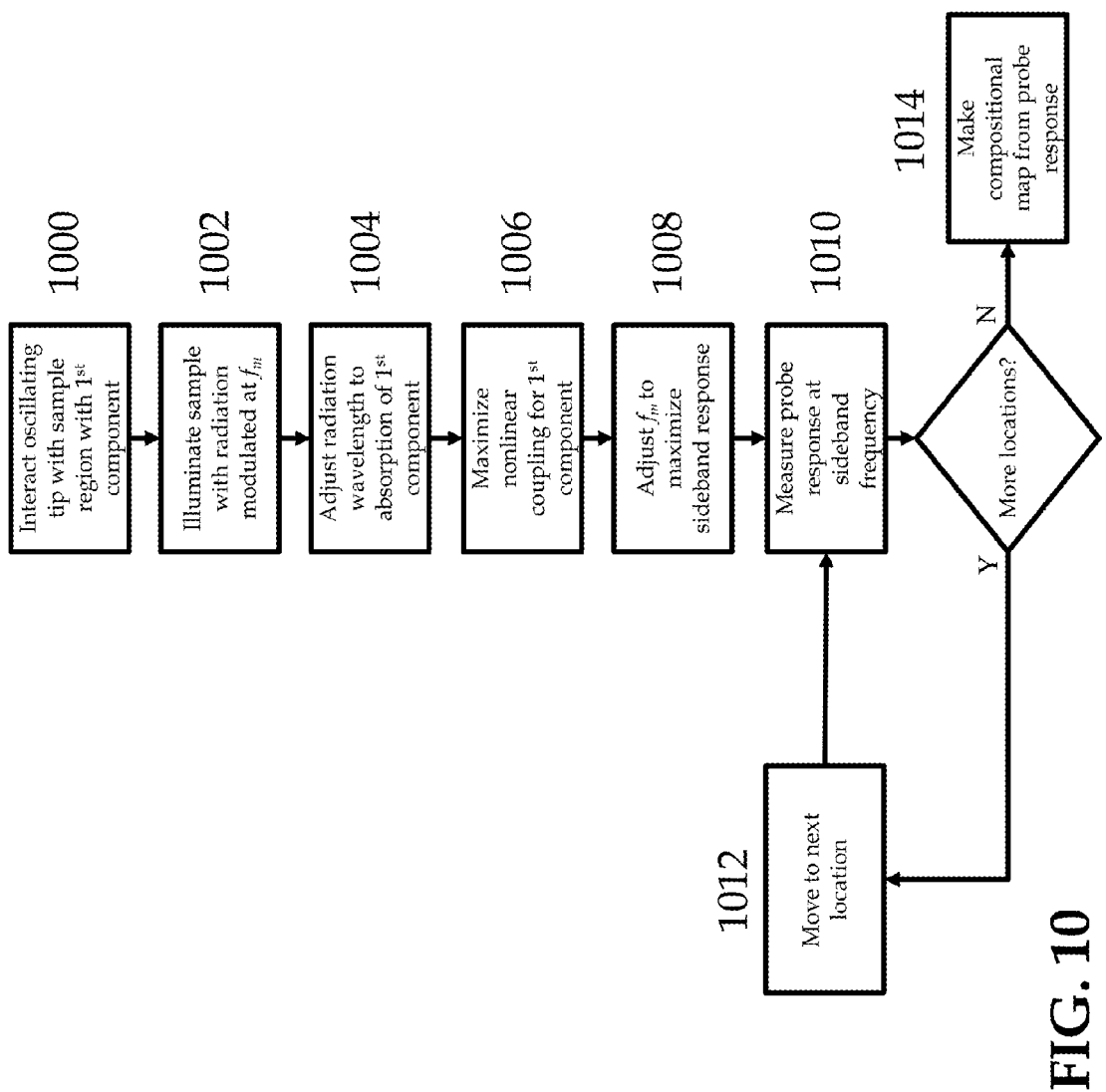
FIG. 10 illustrates a method for using material selective operating parameters to create a map of the distribution of one or more target materials in a heterogeneous sample.

FIG. 10 shows a method for achieving compositional images that are highly selective to a specific material component in a heterogeneous sample. This method is similar to previously described methods in many ways except that it is specifically tuned to be selective to a specific material component. In step 1000, an oscillating probe tip is interacted with the surface of a sample over a $1^{st}$ material component. A survey scan may be completed first to select a region with a specific material of interest. An AFM-IR spectrum may also be obtained to perform chemical analysis of the selected material component. In step 1002, the sample is illuminated with a beam of radiation modulated at a frequency $f_m$. The following three steps 1004, 1006, and 1008 involve the determination of a set of system operating values that produce a substantially maximum probe response on a selected material component. These so called "material selective operating parameters" are then used to tune the system to have a probe response to be highly sensitive to the target material and substantially less sensitive to other material components. In step 1004 the wavelength of the radiation source is adjusted such that it prompts a maximal optical response in the sample. For example, the wavelength can be tuned to a strong absorption band of the target material. Alternately, it can be tuned to a wavelength that maximally discriminates between the selected material component and other material components in the sample. In step 1006, one or more probe interaction parameters adjusted to maximize the nonlinear coupling coefficient, i.e. the γ term in Eq. 7. This can be maximized by measuring the probe response on the selected material component while maximizing the sideband response, or it can be adjusted by using a proxy signal, for example the tapping phase signal as mentioned previously. Next, in step 1008, the modulation frequency of the radiation source is adjusted to achieve a maximum sideband response. In practice this step is adjusting a sideband frequency between the probe oscillation and the light source modulation such that it substantially overlaps with a resonance of the probe while it interacts with the target material. As mentioned previously and illustrated in FIGS. 4 and 5, the probe resonance can be highly sensitive to the material property and as such is also a material selective parameter. Finally, with the set of material selective operating parameters determined and selected to a specific material component, the probe response can be measured at a plurality of locations (steps 1010 and 1012). When the probe response has been measured at the desired number of locations, a compositional map of the sample can be constructed (step 1014). In this case, the map will show a high signal strength when the probe tip is over the selected material and a lower or negligible response over other material components. The entire method can then be repeated for different material components to create maps for the distribution of other materials. The component maps can be overlayed to visualize the relative distribution of different material components. In one embodiment, the values of the material selective operating parameters can be rapidly shifted between values for two or more materials, for example on alternating lines of an image measurement process. For example, when the probe is moving in one direction, e.g. in the trace direction, the material selective operating parameters can be adjusted to be highly sensitive to a first material. Then on the opposite direction, e.g. retrace, the material selective operating parameters can be adjusted to be highly sensitive to another material component. These interleaved measurements can then be used to construct separate or overlay maps of the distribution of two different components. This can be extended as necessary for as many material components are desired to be mapped, for example alternating between material selective operating parameters on successive scan lines. Alternately, it is possible to create ratiometric images that display the relative intensity of the probe response at one radiation wavelength versus another.

Figure 11:
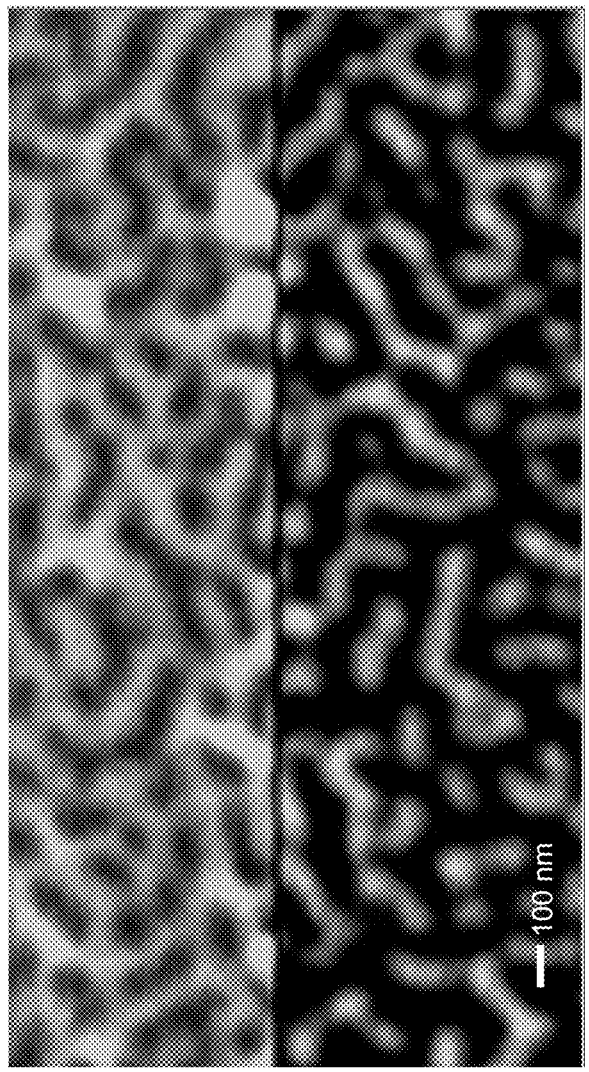
FIG. 11 shows measurement data of resolution and sensitivity enhanced AFM-IR under the method described in FIG. 10.

FIG. 11 shows images created via the process described above in FIG. 10. FIG. 11 shows a resolution and sensitivity enhanced AFM-IR images of a block co-polymer of polystyrene (PS) and poly-methylmethacrylate (PMMA) components. For this image, the material selective operation parameters were switched in the middle of the image to demonstrate the ability to highlight a specific target material. The material selective operation parameters radiation wavelength, modulation frequency and tip interaction parameters. In the upper part of the image, material selective operation parameters are set to selectively enhance the sensitivity to the PS component. In the lower part of the image, the material selective parameters were set to selectively enhance the sensitivity to the other component, PMMA. Notice the contrast reversal that occurs as the parameters are adjusted for a specific material.

Figure 12:
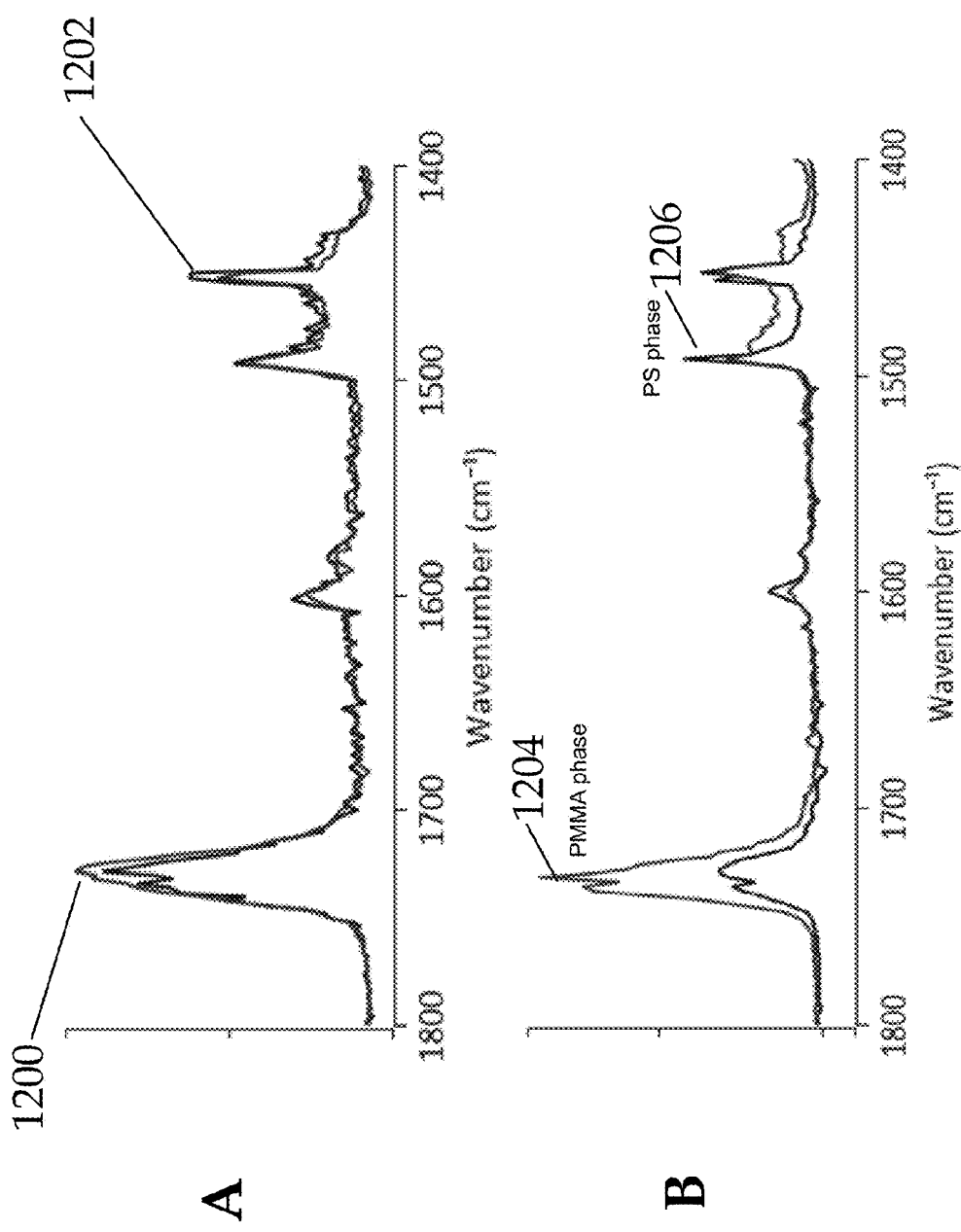

FIG. 12A shows conventional AFM-IR spectra (1200 and 1202) and resolution enhanced AFM-IR spectra (1204 and 1206) obtained using methods described here-in on the PS/PMMA copolymer sample of FIG. 11. FIG. 12A shows one spectrum 1200 measured on PMMA and another 1202 measured on a PS domain area. Because of the very small size of these domains, in the range of 50-100 nm, the difference between these spectra are minimal. Both spectra are substantially contaminated by absorption bands in surrounding material due to thermal diffusions of the heat from IR absorption and/or from absorption of light by domains of the complementary material below the sample surface. FIG. 12B shows resolution enhanced spectra 1204 on PMMA and 1206 on PS that significantly improve the spectral discrimination of these two materials. With this resolution improvement it is possible to obtain spectra with much lower cross-talk even for domains that are smaller than 50-100 nm.

In one embodiment, the IR source 114 of FIG. 1 may be a broadband light source rather than a narrowband source, for example an attosecond, femtosecond or picosecond source, a supercontinuum laser, difference frequency generation, or sum frequency generation source, frequency comb, a globar, and/or thermal source, for example. In this case the output of the light source may contain a broad range of wavelengths and simultaneously excite multiple absorption bands or optical resonances in the sample. In this case the radiation from the IR source 114 may pass through an interferometer being incident on the sample. The interferometer may be used to demodulate the wavelength dependent probe response. The interferometer may comprise two arms with a fixed mirror in one arm and a moving mirror in the other. By sweeping the moving mirror the relative optical phase of the interferometer is swept to create a probe response interferogram that can then be Fourier transformed into a spectrum that reveals the probe response as a function of wavenumber or equivalently wavelength. The wavelength dependent probe response can be indicative of an optical response of the region of the sample under the probe tip.

Note that the methods described in this specification can also work with a sample immersed in liquid, including aqueous solutions. Although the probe quality factor may be reduced due to liquid damping and added mass effects, the basic technique for resolution and sensitivity enhanced AFM-IR is still applicable. In this case it is desirable to choose a cantilever probe that substantially minimizes the fluid mass that is "carried" by the oscillating cantilever and/or minimizing the viscous damping force of the cantilever moving through the liquid. Additionally, T-shaped cantilevers that excite torsional resonance modes or cantilever geometries that excite lateral oscillation modes can reduce one or both of the effects of carried mass and viscous damping. For example, some AFM probes have been designed to work where the AFM tip itself is immersed in liquid, while the body of the cantilever can be oscillated in air. Minary-Jolandan et al (Nanotechnology 23 (2012) 235704) describe an AFM probe with a long needle tip that can be immersed in a liquid while the cantilever remains in air. High Q fluid cantilevers have also been made with immersible reservoirs surrounding the cantilever portion that maintain the lever in air with the tip in liquid, for example Yu et al. (Lab Chip, 2016, 16, 902-910) and by the commercial company Scuba Probe and described in U.S. Pat. No. 9,229,028. Lateral mode cantilevers with low damping and high Q have been demonstrated Tao et al. ("High-Q in-plane resonance-mode cantilever bio/chemical sensor for real-time detection in liquids," in: Solid-State Sensors, Actuators and Microsystems Conference (TRANSDUCERS), 2011 16th International, DOI 10.1109/TRANSDUCERS.2011.5969319). Using any of these techniques it is possible to achieve a quality factor in liquid in excess of 100, sufficient for high quality resolution and sensitivity enhanced AFM-IR. Even in cases where the quality factor Q may be reduced, the other contributors to the signal, i.e. the sample thermal expansion and the non-linear tip/sample coupling can still be appreciable and thus the techniques mentioned in this application for selecting material specific operating parameters can still apply.

The embodiments described herein are exemplary. Modifications, rearrangements, substitute processes, alternative elements, etc. may be made to these embodiments and still be encompassed within the teachings set forth herein. One or more of the steps, processes, or methods described herein may be carried out by one or more processing and/or digital devices, suitably programmed.

Depending on the embodiment, certain acts, events, or functions of any of the method steps described herein can be performed in a different sequence, can be added, merged, or left out altogether (e.g., not all described acts or events are necessary for the practice of the algorithm). Moreover, in certain embodiments, acts or events can be performed concurrently, rather than sequentially.

The various illustrative logical blocks, optical and SPM control elements, and method steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processor configured with specific instructions, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The elements of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable storage medium known in the art. An exemplary storage medium can be coupled to the processor such that the processor can read information from, and write information to, the storage medium. In the alternative, the storage medium can be integral to the processor. The processor and the storage medium can reside in an ASIC. A software module can comprise computer-executable instructions which cause a hardware processor to execute the computer-executable instructions.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y or Z," unless specifically stated otherwise, is otherwise understood with the context as used in general to present that an item, term, etc., may be either X, Y or Z, or any combination thereof (e.g., X, Y and/or Z). Thus, such disjunctive language is not generally intended to, and should not, imply that certain embodiments require at least one of X, at least one of Y or at least one of Z to each be present.

The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a result (e.g., measurement value) is close to a targeted value, where close can mean, for example, the result is within 80% of the value, within 90% of the value, within 95% of the value, or within 99% of the value.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to illustrative embodiments, it will be understood that various omissions, substitutions, and changes in the form and details of the devices or methods illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

We claim:

1. A method of mapping a surface of a heterogeneous sample with a probe of a scanning probe microscope, comprising the steps of:
   a. Oscillating the probe at a first frequency $f_1$;
   b. Interacting the probe with a first region of the sample;
   c. Illuminating the sample with a beam of infrared radiation;
   d. Modulating the beam of infrared radiation at frequency $f_m$ such that a resulting sideband frequency $f_{sb}$ is substantially equal to a resonance of the probe while interacting with a sample material at the first region;
   e. Measuring a probe response at the first region of the sample at the sideband frequency due to infrared radiation incident on the sample;
   f. Moving the probe to interact with a second region of a sample resulting in a shift in a resonance of the probe;
   g. Retuning the modulation frequency $f_m$ resulting in a shifted sideband frequency that is substantially equal to the shifted probe resonance;
   h. Measuring a probe response at the shifted sideband frequency on the second region due to infrared radiation incident on the sample; and
   i. Creating a compositional map of the sample based on the measured probe responses, wherein the compositional map has a spatial resolution of <10 nm.

2. The method of claim 1 further comprising the step of adjusting probe interaction parameters to substantially maximize a contrast between the probe responses on the first and second regions.

3. The method of claim 1 wherein the step of retuning the modulation frequency is performed automatically.

4. The method of claim 1 further comprising the step of measuring a phase of oscillation of the probe while the probe is in interaction with the sample region.

5. The method of claim 4 further comprising the step of using the phase measurement to adjust the radiation modulation frequency $f_m$.

6. The method of claim 4 further comprising the step of adjusting a parameter of probe interaction to substantially maximize a contrast in the phase measurement between two or more material components in the sample.

7. The method of claim 1 wherein the frequency $f_1$ substantially corresponds to a probe resonance.

8. The method of claim 1 wherein the sample region is immersed in a liquid.

9. A method of mapping a surface of a heterogeneous sample, the method comprising the steps of:
   a. Oscillating the probe at a first frequency $f_1$;
   b. Interacting a probe of a probe microscope with a first region of the sample;
   c. Illuminating the sample with a beam of infrared radiation;
   d. Modulating the beam of infrared radiation at frequency $f_m$ such that a resulting sideband frequency $f_{sb}$ is substantially equal to a resonance of the probe while interacting with a sample material at the first region;
   e. Measuring a probe response to infrared radiation incident on the first region of the sample at the sideband frequency;
   f. Moving the probe to interacting with a second region of a sample;
   g. Retuning the modulation frequency $f_m$ resulting in a shifted sideband frequency that is substantially equal to a resonance of the probe while interacting with a sample material at the second region of the sample;
   h. Measuring a probe response to infrared radiation incident on the second region of the sample at the shifted sideband frequency; and
   i. Creating a compositional map of the sample based on the measured probe responses, wherein the compositional map has a spatial resolution of <10 nm.

10. A method of mapping a surface of a heterogeneous sample with a probe of a scanning probe microscope, comprising the steps of:
    a. Oscillating the probe at a first frequency $f_1$;
    b. Interacting the probe with a first region of the sample;
    c. Illuminating the sample with a beam of infrared radiation;
    d. Modulating the beam of infrared radiation at frequency $f_m$ such that a resulting sideband frequency $f_{sb}$ is substantially equal to a resonance of the probe while interacting with a sample material at the first region;
    e. Measuring a probe response at the first region of the sample at the sideband frequency due to infrared radiation incident on the sample;
    f. Moving the probe to interact with a second region of a sample resulting in a shift in a resonance of the probe;
    g. Retuning the modulation frequency $f_m$ resulting in a shifted sideband frequency that is substantially equal to the shifted probe resonance;
    h. Measuring a probe response at the shifted sideband frequency on the second region due to infrared radiation incident on the sample;
    i. Measuring a phase of oscillation of the probe while the probe is in interaction with the sample region; and
    j. Adjusting a parameter of probe interaction to substantially maximize a contrast in the phase measurement between two or more material components in the sample.

11. The method of claim 10 further comprising the step of creating a compositional map of the sample based on the measured probe responses.

12. The method of claim 11 wherein the compositional map has a spatial resolution of <10 nm.

13. The method of claim 10 further comprising the step of adjusting probe interaction parameters to substantially maximize a contrast between the probe responses on the first and second regions.

14. The method of claim 10 wherein the step of retuning the modulation frequency is performed automatically.

15. The method of claim 10 further comprising the step of using the phase measurement to adjust the radiation modulation frequency $f_m$.

16. The method of claim 10 wherein the frequency $f_1$ substantially corresponds to a probe resonance.

17. The method of claim 10 wherein the sample region is immersed in a liquid.

* * * * *